US012590290B2

(12) United States Patent
Hsu

(10) Patent No.: US 12,590,290 B2
(45) Date of Patent: Mar. 31, 2026

(54) METHOD FOR TREATING AND MODELLING HEARING LOSS

(71) Applicant: Yi-Chao Hsu, New Taipei City (TW)

(72) Inventor: Yi-Chao Hsu, New Taipei City (TW)

(73) Assignee: Mackay Medical College, New Taipei City (TW)

( * ) Notice: Subject to any disclaimer, the term of this patent is extended or adjusted under 35 U.S.C. 154(b) by 1262 days.

(21) Appl. No.: 17/052,818

(22) PCT Filed: Apr. 30, 2019

(86) PCT No.: PCT/CN2019/085289
§ 371 (c)(1),
(2) Date: Nov. 4, 2020

(87) PCT Pub. No.: WO2019/210858
PCT Pub. Date: Nov. 7, 2019

(65) Prior Publication Data
US 2021/0130772 A1 May 6, 2021

Related U.S. Application Data

(60) Provisional application No. 62/666,952, filed on May 4, 2018.

(51) Int. Cl.
*C12N 5/0793* (2010.01)

(52) U.S. Cl.
CPC ........ *C12N 5/062* (2013.01); *C12N 2501/998* (2013.01)

(58) Field of Classification Search
CPC ............................ C12N 2501/00; C12N 5/062
See application file for complete search history.

(56) References Cited

U.S. PATENT DOCUMENTS

2009/0098093 A1* 4/2009 Edge ...................... A61K 35/12
424/93.7

OTHER PUBLICATIONS

Chen et al. (Apr. 19, 2018) "ATOH1/RFX1/RFX3 transcription factors facilitate the differentiation and characterisation of inner ear hair cell-like cells from patient-specific induced pluripotent stem cells harbouring A8344G mutation of mitochondrial DNA" Cell Death & Disease, 9(4), 437, 15 pages. (Year: 2018).*

Schimmang, Thomas (2013) "Transcription factors that control inner ear development and their potential for transdifferentiation and reprogramming" Hearing research, 297, 84-90. (Year: 2013).*

Elkon et al. (2015) "RFX transcription factors are essential for hearing in mice" Nature communications, 6(1), 8549. (Year: 2015).*

Wang et al. "Intercellular Junctions Between Hair Cell-like Cells and Supporting Cells Derived from Human iPSCs" Chinese Journal of Otology, No. 4, Aug. 31, 2017. (Year: 2017).*

Costa et al. (2015) "Generation of sensory hair cells by genetic programming with a combination of transcription factors" Development, 142(11), 1948-1959. (Year: 2015).*

Gettelfinger et al. (Jan. 4, 2018) "Syndromic hearing loss: a brief review of common presentations and genetics" Journal of pediatric genetics, 7(01), 001-008. (Year: 2018).*

Chou et al. (2016) "Impaired ROS scavenging system in human induced pluripotent stem cells generated from patients with MERRF syndrome" Scientific reports, 6(1), 23661, 14 pages. (Year: 2016).*

Ronaghi et al. (2014) "Inner ear hair cell-like cells from human embryonic stem cells" Stem cells and development, 23(11), 1275-1284. (Year: 2014).*

International Search Report and Written Opinion for International Application No. PCT/CN2019/085289 mailed on Aug. 5, 2019, 7 pages.

Wang, et al. "Intercellular Junctions Between Hair Cell-like Cells and Supporting Cells Derived From Human iPSCs", Chinese Journal of Otology, No. 4, Aug. 31, 2017.

Izumikawa, et al. "Auditory hair cell replacement and hearing improvement by Atoh1 gene therapy in deaf mammals", Nature Medicine, vol. 11, Feb. 13, 2005.

Elkon, et al. "RFX transcription factors are essential for hearing in mice", Nature Communications, vol. 6, Oct. 15, 2015.

* cited by examiner

*Primary Examiner* — James Joseph Graber

(74) *Attorney, Agent, or Firm* — Amin, Turocy & Watson, LLP

(57) ABSTRACT

A method for treating hearing loss in a subject in need thereof is provided. The method includes providing a combination of transcription factors to induce generation of a hair cell-like cell, thereby treating the hearing loss in the subject. The generated hair cell-like cells exhibit characteristic of mature functional cells that is useful in cell replacement therapy for autologous transplantation.

13 Claims, 23 Drawing Sheets

Specification includes a Sequence Listing.

SEQUENCE LISTING

<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: SOX2-F
<220> FEATURE:
<221> NAME/KEY: primer_bind
<222> LOCATION: (1)..(21)

<400> SEQUENCE: 1
tacagcatgt cctactcgca g                                                              21

<210> SEQ ID NO 2
<211> LENGTH: 21
<212> TYPE: DNA
<213> ORGANISM: Artificial Sequence
<220> FEATURE:
<223> OTHER INFORMATION: SOX2-R
<220> FEATURE:
<221> NAME/KEY: primer_bind
<222> LOCATION: (1)..(21)

<400> SEQUENCE: 2
gaggaagagg taaccacagg g                                                              21

<210> SEQ ID NO 3
<211> LENGTH: 21
<212> TYPE: DNA
<213> ORGANISM: Artificial Sequence
<220> FEATURE:
<223> OTHER INFORMATION: OCT4-F
<220> FEATURE:
<221> NAME/KEY: primer_bind
<222> LOCATION: (1)..(21)

<400> SEQUENCE: 3
cttcaggcac tgtgttcatt g                                                              21

<210> SEQ ID NO 4
<211> LENGTH: 20
<212> TYPE: DNA
<213> ORGANISM: Artificial Sequence
<220> FEATURE:
<223> OTHER INFORMATION: OCT4-R
<220> FEATURE:
<221> NAME/KEY: primer_bind
<222> LOCATION: (1)..(20)

<400> SEQUENCE: 4
tttggctgaa caccttccca                                                                20

<210> SEQ ID NO 5
<211> LENGTH: 21
<212> TYPE: DNA
<213> ORGANISM: Artificial Sequence
<220> FEATURE:
<223> OTHER INFORMATION: NANOG-F
<220> FEATURE:
<221> NAME/KEY: primer_bind
<222> LOCATION: (1)..(21)

<400> SEQUENCE: 5
aaggtcccgg tcaagaaaca g                                                              21

<210> SEQ ID NO 6

```
<211> LENGTH: 20
<212> TYPE: DNA
<213> ORGANISM: Artificial Sequence
<220> FEATURE:
<223> OTHER INFORMATION: NANOG-R
<220> FEATURE:
<221> NAME/KEY: primer_bind
<222> LOCATION: (1)..(20)

<400> SEQUENCE: 6
cttctgcgtc acaccattgc                                                    20

<210> SEQ ID NO 7
<211> LENGTH: 21
<212> TYPE: DNA
<213> ORGANISM: Artificial Sequence
<220> FEATURE:
<223> OTHER INFORMATION: GATA6-F
<220> FEATURE:
<221> NAME/KEY: primer_bind
<222> LOCATION: (1)..(21)

<400> SEQUENCE: 7
ctcagttcct acgcttcgca t                                                  21

<210> SEQ ID NO 8
<211> LENGTH: 20
<212> TYPE: DNA
<213> ORGANISM: Artificial Sequence
<220> FEATURE:
<223> OTHER INFORMATION: GATA6-R
<220> FEATURE:
<221> NAME/KEY: primer_bind
<222> LOCATION: (1)..(20)

<400> SEQUENCE: 8
gtcgaggtca gtgaacagca                                                    20

<210> SEQ ID NO 9
<211> LENGTH: 23
<212> TYPE: DNA
<213> ORGANISM: Artificial Sequence
<220> FEATURE:
<223> OTHER INFORMATION: Brachyury-F
<220> FEATURE:
<221> NAME/KEY: primer_bind
<222> LOCATION: (1)..(23)

<400> SEQUENCE: 9
tatgagcctc gaatccacat agt                                                23

<210> SEQ ID NO 10
<211> LENGTH: 22
<212> TYPE: DNA
<213> ORGANISM: Artificial Sequence
<220> FEATURE:
<223> OTHER INFORMATION: Brachyury-R
<220> FEATURE:
<221> NAME/KEY: primer_bind
<222> LOCATION: (1)..(22)

<400> SEQUENCE: 10
cctcgttctg ataagcagtc ac                                                 22

<210> SEQ ID NO 11
<211> LENGTH: 20
<212> TYPE: DNA
<213> ORGANISM: Artificial Sequence
<220> FEATURE:
```

<223> OTHER INFORMATION: SIX1-F
<220> FEATURE:
<221> NAME/KEY: primer_bind
<222> LOCATION: (1)..(20)

<400> SEQUENCE: 11
ctgccgtcgt ttggctttac                                              20

<210> SEQ ID NO 12
<211> LENGTH: 20
<212> TYPE: DNA
<213> ORGANISM: Artificial Sequence
<220> FEATURE:
<223> OTHER INFORMATION: SIX1-R
<220> FEATURE:
<221> NAME/KEY: primer_bind
<222> LOCATION: (1)..(20)

<400> SEQUENCE: 12
gctctcgttc ttgtgcaggt                                              20

<210> SEQ ID NO 13
<211> LENGTH: 21
<212> TYPE: DNA
<213> ORGANISM: Artificial Sequence
<220> FEATURE:
<223> OTHER INFORMATION: EYA1-F

<400> SEQUENCE: 13
gtcacagtct cagtcacctg g                                            21

<210> SEQ ID NO 14
<211> LENGTH: 22
<212> TYPE: DNA
<213> ORGANISM: Artificial Sequence
<220> FEATURE:
<223> OTHER INFORMATION: EYA1-R
<220> FEATURE:
<221> NAME/KEY: primer_bind
<222> LOCATION: (1)..(22)

<400> SEQUENCE: 14
gggataagac ggatagtcct gc                                           22

<210> SEQ ID NO 15
<211> LENGTH: 20
<212> TYPE: DNA
<213> ORGANISM: Artificial Sequence
<220> FEATURE:
<223> OTHER INFORMATION: PAX2-F
<220> FEATURE:
<221> NAME/KEY: primer_bind
<222> LOCATION: (1)..(20)

<400> SEQUENCE: 15
cggctgtgtc agcaaaatcc                                              20

<210> SEQ ID NO 16
<211> LENGTH: 18
<212> TYPE: DNA
<213> ORGANISM: Artificial Sequence
<220> FEATURE:
<223> OTHER INFORMATION: PAX2-R
<220> FEATURE:
<221> NAME/KEY: primer_bind
<222> LOCATION: (1)..(18)

<400> SEQUENCE: 16

-continued gcttggagcc accgatca                                                       18

<210> SEQ ID NO 17
<211> LENGTH: 21
<212> TYPE: DNA
<213> ORGANISM: Artificial Sequence
<220> FEATURE:
<223> OTHER INFORMATION: PAX6-F
<220> FEATURE:
<221> NAME/KEY: primer_bind
<222> LOCATION: (1)..(21)

<400> SEQUENCE: 17
tgggcaggta ttacgagact g                                                   21

<210> SEQ ID NO 18
<211> LENGTH: 21
<212> TYPE: DNA
<213> ORGANISM: Artificial Sequence
<220> FEATURE:
<223> OTHER INFORMATION: PAX6-R
<220> FEATURE:
<221> NAME/KEY: primer_bind
<222> LOCATION: (1)..(21)

<400> SEQUENCE: 18
actcccgctt atactgggct a                                                   21

<210> SEQ ID NO 19
<211> LENGTH: 22
<212> TYPE: DNA
<213> ORGANISM: Artificial Sequence
<220> FEATURE:
<223> OTHER INFORMATION: DLX5-F
<220> FEATURE:
<221> NAME/KEY: primer_bind
<222> LOCATION: (1)..(22)

<400> SEQUENCE: 19
gtcttcagct accgattctg ac                                                  22

<210> SEQ ID NO 20
<211> LENGTH: 20
<212> TYPE: DNA
<213> ORGANISM: Artificial Sequence
<220> FEATURE:
<223> OTHER INFORMATION: DLX5-R
<220> FEATURE:
<221> NAME/KEY: primer_bind
<222> LOCATION: (1)..(20)

<400> SEQUENCE: 20
ctttgccata ggaagccgag                                                     20

<210> SEQ ID NO 21
<211> LENGTH: 19
<212> TYPE: DNA
<213> ORGANISM: Artificial Sequence
<220> FEATURE:
<223> OTHER INFORMATION: MYO7A-F
<220> FEATURE:
<221> NAME/KEY: primer_bind
<222> LOCATION: (1)..(19)

<400> SEQUENCE: 21
gcagaacgca acgcacatc                                                      19

<210> SEQ ID NO 22

-continued

```
<211> LENGTH: 19
<212> TYPE: DNA
<213> ORGANISM: Artificial Sequence
<220> FEATURE:
<223> OTHER INFORMATION: MYO7A-R
<220> FEATURE:
<221> NAME/KEY: primer_bind
<222> LOCATION: (1)..(19)

<400> SEQUENCE: 22
tcccggtagc ggataagca                                                    19

<210> SEQ ID NO 23
<211> LENGTH: 19
<212> TYPE: DNA
<213> ORGANISM: Artificial Sequence
<220> FEATURE:
<223> OTHER INFORMATION: RFX1-F
<220> FEATURE:
<221> NAME/KEY: primer_bind
<222> LOCATION: (1)..(19)

<400> SEQUENCE: 23
agaccggcgt tcctactca                                                    19

<210> SEQ ID NO 24
<211> LENGTH: 20
<212> TYPE: DNA
<213> ORGANISM: Artificial Sequence
<220> FEATURE:
<223> OTHER INFORMATION: RFX1-R
<220> FEATURE:
<221> NAME/KEY: primer_bind
<222> LOCATION: (1)..(20)

<400> SEQUENCE: 24
gcagcgtagt ggataggcag                                                   20

<210> SEQ ID NO 25
<211> LENGTH: 20
<212> TYPE: DNA
<213> ORGANISM: Artificial Sequence
<220> FEATURE:
<223> OTHER INFORMATION: RFX2-F
<220> FEATURE:
<221> NAME/KEY: primer_bind
<222> LOCATION: (1)..(20)

<400> SEQUENCE: 25
gcgattgaaa acctccaaaa                                                   20

<210> SEQ ID NO 26
<211> LENGTH: 20
<212> TYPE: DNA
<213> ORGANISM: Artificial Sequence
<220> FEATURE:
<223> OTHER INFORMATION: RFX2-R
<220> FEATURE:
<221> NAME/KEY: primer_bind
<222> LOCATION: (1)..(20)

<400> SEQUENCE: 26
ggcttcagac gaatcccata                                                   20

<210> SEQ ID NO 27
<211> LENGTH: 20
<212> TYPE: DNA
<213> ORGANISM: Artificial Sequence
<220> FEATURE:
```

<223> OTHER INFORMATION: RFX3-F
<220> FEATURE:
<221> NAME/KEY: primer_bind
<222> LOCATION: (1)..(20)

<400> SEQUENCE: 27
aaactggacc cagtcaatgc                                              20

<210> SEQ ID NO 28
<211> LENGTH: 20
<212> TYPE: DNA
<213> ORGANISM: Artificial Sequence
<220> FEATURE:
<223> OTHER INFORMATION: RFX3-R
<220> FEATURE:
<221> NAME/KEY: primer_bind
<222> LOCATION: (1)..(20)

<400> SEQUENCE: 28
tgttgcatgg gttgttgtct                                              20

<210> SEQ ID NO 29
<211> LENGTH: 21
<212> TYPE: DNA
<213> ORGANISM: Artificial Sequence
<220> FEATURE:
<223> OTHER INFORMATION: ESPN-F
<220> FEATURE:
<221> NAME/KEY: primer_bind
<222> LOCATION: (1)..(21)

<400> SEQUENCE: 29
cagagtgcag gacaaagaca a                                            21

<210> SEQ ID NO 30
<211> LENGTH: 20
<212> TYPE: DNA
<213> ORGANISM: Artificial Sequence
<220> FEATURE:
<223> OTHER INFORMATION: ESPN-R
<220> FEATURE:
<221> NAME/KEY: primer_bind
<222> LOCATION: (1)..(20)

<400> SEQUENCE: 30
gcagcgtagt ggataggcag                                              20

<210> SEQ ID NO 31
<211> LENGTH: 22
<212> TYPE: DNA
<213> ORGANISM: Artificial Sequence
<220> FEATURE:
<223> OTHER INFORMATION: GAPDH-F
<220> FEATURE:
<221> NAME/KEY: primer_bind
<222> LOCATION: (1)..(22)

<400> SEQUENCE: 31
tggtggcagt taccttacta ct                                           22

<210> SEQ ID NO 32
<211> LENGTH: 21
<212> TYPE: DNA
<213> ORGANISM: Artificial Sequence
<220> FEATURE:
<223> OTHER INFORMATION: GAPDH-R
<220> FEATURE:
<221> NAME/KEY: primer_bind
<222> LOCATION: (1)..(21)

-continued

```
<400> SEQUENCE: 32
caagggctct tgatttgctg a                                    21
```

METHOD FOR TREATING AND MODELLING HEARING LOSS

BACKGROUND

1. Field of the Disclosure

The present disclosure relates to methods for treating hearing loss, and more particularly, relates to methods for generation of hair cell (HC)-like cells from otic progenitor cells derived from human stem cells in vitro and in human cochlear tissues in vivo. The methods are applicable in direct reprogramming of HC-like cells from somatic cells or tissues.

2. Description of Related Art

Degeneration or loss of inner ear HCs is irreversible and results in sensorineural hearing loss (SHL). To treat the hearing loss, it holds a great potential in cell replacement therapy where HCs are regenerated and delivered to the patients.

To regenerate inner ear HCs, mouse bone-marrow mesenchymal stem cells (MSCs) are the first to be differentiated into HC-like cells. In addition, embryonic stem cells (ESCs) and induced pluripotent stem cells (iPSCs), which have been employed in disease modelling and cell therapy as the source of the cells for differentiation into various specialized cells, are also considered as the promising cell sources for regenerating HCs. (1, 2) Indeed, mouse ESCs and iPSCs have been shown to differentiate into mechanosensitive HC-like cells. (3) However, although it appears to be a useful approach, the use of chicken utricle stromal cells to induce HC differentiation in such approach may cause cell culture contamination and limit the future clinical application.

Recently, human ESCs were also found to differentiate into otic progenitors (OPs) and then spontaneously into HC-like cells, which exhibit many features of nascent HCs but fail to become mature HCs. (4)

Proneural protein atonal homolog 1 (ATOH1) is a transcription factor (TF) that regulates differentiation of HCs. Ectopic expression of Atoh1 induced in bone-marrow MSCs leads to HC differentiation with a distinct morphology and expression of HC markers such as Myo7A (MYO7A) and espin (ESPN). (1, 5) Furthermore, ectopic expression of ATOH1 in human umbilical cord MSCs can lead to the differentiation of inner ear HC-like cells. (6) Recently, increasing evidence indicates that ATOH1 gene therapy is effective against SHL in animals (7-9) and is currently the focus of a phase I/II clinical trial initiated by Novartis Pharmaceuticals for patients with bilateral severe-to-profound SHL. (10) However, ATOH1-differentiated HCs are still immature both molecularly and electrophysiologically in vivo, indicating the unmet need for HC differentiation. (11)

SUMMARY OF THE DISCLOSURE

Herein, it is surprisingly found that ciliogenic TF, regulatory factor for the x-box (RFX), exerts regulatory effects on the differentiation of HC-like cells from human stem cells and on the direct reprogramming of HC-like cells from somatic cells; particularly, it was found that RFX1/RFX3 cooperated with ATOH1 can efficiently promote the differentiation of iPSCs into HC-like cells more than ATOH1 alone.

In an aspect of the present disclosure, a method for treating hearing loss in a subject in need thereof is provided. The method comprises providing a set of nucleic acids or a set of polypeptides for inducing generation of a mature HC-like cell, wherein the set of nucleic acids comprises a first nucleic acid encoding ATOH1, a second nucleic acid encoding RFX1, and a third nucleic acid encoding RFX3, and wherein the set of polypeptides comprises ATOH1, RFX1, and RFX3.

In an embodiment of the present disclosure, the generation of the mature HC-like cell is driven by differentiation of an otic progenitor cell, or by direct reprogramming from a somatic cell of the subject.

In an embodiment of the present disclosure, the otic progenitor cell may be in the inner ear of the subject. In another embodiment of the present disclosure, the otic progenitor cell may be derived from iPSC or ESC.

In an embodiment of the present disclosure, the method further comprises obtaining a somatic cell from the subject for producing an iPSC. In another embodiment of the present disclosure, the method further comprises differentiating the iPSC into the otic progenitor cell. In yet another embodiment of the present disclosure, the method further comprises delivering the differentiated mature HC-like cell into an inner ear of the subject.

In an embodiment of the present disclosure, the method further comprises obtaining a somatic cell from the subject for direct reprogramming from the somatic cell to produce HC-like cells. In another embodiment of the present disclosure, the somatic cell can be a skin fibroblast or a peripheral blood mononuclear cell.

In an embodiment of the present disclosure, the differentiation of the iPSC into the otic progenitor cell and the HC-like cell is in the absence of a feeder cell.

In an embodiment of the present disclosure, the mature HC-like cell has stereociliary bundles on the cell surface thereof.

In an embodiment of the present disclosure, the subject suffers from the hearing loss involving degeneration or loss of inner ear hair cells. In another embodiment of the present disclosure, the subject suffers from sensorineural hearing loss.

In an embodiment of the present disclosure, the mature hair cell-like cell serves as a modelling system for the hearing loss. In another embodiment of the present disclosure, the method further provides a disease modelling system by using the iPSCs of the subject with deafness gene mutations, such as nuclear gene mutations or mitochondrial DNA (mtDNA) mutation, wherein the iPSCs are differentiated into HC-like cells by ATOH1/RFX1/RFX3.

In another aspect of the present disclosure, a method for generating an inner ear hair cell from a pluripotent stem cell in vitro is provided. The method comprises differentiating the pluripotent stem cell into an otic progenitor cell; and culturing the otic progenitor cell in the presence of a set of nucleic acids or a set of polypeptides for an otic progenitor cell to obtain a population comprising the inner ear hair cell, wherein the set of nucleic acids comprises a first nucleic acid encoding ATOH1, a second nucleic acid encoding RFX1, and a third nucleic acid encoding RFX3, and wherein the set of polypeptides comprises ATOH1, RFX1, and RFX3.

In an embodiment of the present disclosure, the otic progenitor cell is cultured in the absence of a feeder cell to obtain the inner ear hair cell.

In an embodiment of the present disclosure, the inner ear cell is positive for at least one of myosin 7a and espin.

In an embodiment of the present disclosure, the pluripotent stem cell is a human induced pluripotent stem cell (hiPSC). In another embodiment of the present disclosure, the hiPSC is derived from a subject suffering from hearing loss involving degeneration or loss of inner ear hair cells. In another embodiment of the present disclosure, the hiPSC is derived from a subject suffering from sensorineural hearing loss. In yet another embodiment of the present disclosure, the hiPSC is derived from a somatic cell with nuclear gene mutations or mtDNA point mutation.

In another aspect of the present disclosure, a kit for treating hearing loss is provided. The kit comprises a set of expression vectors including a first expression vector having a first nucleic acid encoding ATOH1; a second expression vector having a second nucleic acid encoding RFX1; and a third expression vector having a third nucleic acid encoding RFX3, wherein the set of expression vectors allows production of transcription factors comprising ATOH1, RFX1, and RFX3 in a host cell. In an embodiment of the present disclosure, the host cell is an otic progenitor cell derived from a hiPSC. In another embodiment of the present disclosure, at least one of the first, second and third expression vectors is a lentiviral vector.

The present disclosure provides a method as a gene therapy or a protein drug against hearing loss. The method of the present disclosure involves the differentiation of the otic progenitor cells in the inner ear of a subject into mature HC-like cells, which is induced in presence of nucleic acids or polypeptides of ATOH1, RFX1, and RFX3. The present disclosure also provides a method to differentiate iPSCs into mature HC-like cells, with which cell therapy against hearing loss can be developed. The present disclosure provides a TF-driven approach for HC differentiation. RFX1/RFX3 TFs in combination with ATOH1 cooperatively and efficiently promote the differentiation of HC-like cells with more mature stereociliary bundles.

The present disclosure provides a method involving the use of RFX1/RFX3/ATOH1 in inducing the differentiation of HC-like cells from hiPSCs that does not involve coculturing with an external cell lineage and therefore avoids cell contamination. The differentiated HC-like cells can be derived from SHL patients' own somatic cells adopting the method of the present disclosure that is effective in cell replacement therapy for autologous transplantation because it would not cause rejection.

The RFX1/RFX3/ATOH1 TFs-driven approach for the differentiation of HC-like cells from hiPSCs of the present disclosure is efficient and promising for disease modelling and can be applied in therapy against SHL.

BRIEF DESCRIPTION OF THE DRAWINGS

The present disclosure contains a Sequence Listing XML which has been submitted electronically in XML format and is hereby incorporated by reference in its entirety. The XML copy, created on Nov. 13, 2025, is named MAMC-0004WOUS-Sequence Listing ST25.txt and is 8,192 bytes in size.

The present disclosure can be more fully understood by reading the following detailed descriptions of the embodiments, with reference made to the accompanying drawings.

FIG. 1A shows schematic illustration of the 42-day otic guidance protocol. KSR represents knockout serum replacement. The hiPSCs show round and flat morphology in bright field (BF). The sphere-like embryoid body (EB) formation is observed on Day 1. Ectodermal differentiation (ED) is observed on Day 15. OPs induction is observed on Day 21. The epithelium-like HCs differentiation is observed on Day 42. Scale bar=50 μm in EB, and 100 μm in ED, OPs, and HCs. FIG. 1B shows semiquantitative reverse transcription polymerase chain reaction (RT-PCR) analyses for the mRNA expression of ATOH1, RFX1, RFX2, and RFX3 genes at different stages (EB, ED, OP and HC) during HC differentiation from hiPSCs and hESCs.

FIG. 2A shows that ESC-specific gene transcripts (SOX2, NANOG, and OCT4) were expressed at the EB stage, non-neural ectoderm-specific genes (SIX1 and EYA1) were expressed at the ED stage, and the endoderm-specific GATA6 gene, OP-specific genes (PAX2 and DLX5), the neural progenitor-specific PAX6 gene, and HC-specific genes (MYO7A and ESPN) were expressed at the HC stage. FIG. 2B shows the numbers of mCherry$^{MYO7A}$-positive cells counted on Days 28, 35, and 42. Data are presented as mean±standard deviation (SD); *p<0.001, p<0.01. Positive cells were counted by randomly selecting five fields in the indicated time-points. FIG. 2C shows colocalisation of MYO7A$^{mCherry}$ with ESPN and FM 1-43-positive cells. Scale bar in ESPN staining is 10 μm, and scale bar in FM 1-43 staining is 25 μm.

FIG. 4A shows the proportion of mtDNA with A8344G mutation that was quantified by pyrosequencing of MERRF iPSCs (M1-iPSCs and M2-iPSCs). FIG. 4B shows quantification of the intracellular ROS levels in MERRF-iPSCs, as indicated by flow cytometry. , p<0.01, N=3. FIG. 4C shows the expression level of the antioxidant enzyme genes in MERRF-iPSCs, demonstrated by quantitative RT-PCR (qRT-PCR). *, p<0.001, N=3.

FIG. 5A shows morphology of M1$^{ctrl}$, M1, and M2 cells during HC differentiation: these iPSCs exhibited a round and flat morphology in the bright field imaging. The whole HC differentiation process included embryoid body (EB) formation, ectoderm differentiation (ED), otic progenitor (OP), and HC differentiation. Scale bar=100 μm. FIGS. 5B to 5D show mRNA expression levels of ATOH1, RFX2, and RFX3 during the differentiation process of M1$^{ctrl}$-, M1- and M2-iPSCs, respectively. FIG. 5E shows quantification of the intracellular ROS levels in M1- and M2-HC-like cells, as indicated by flow cytometry. ***, p<0.001, N=3. FIG. 5F shows the expression level of the antioxidant enzyme genes in M1- and M2-HC-like cells, demonstrated by quantitative RT-PCR (qRT-PCR). *, p<0.05, , p<0.01, *, p<0.001, N=3. FIGS. 5G to 5I show cilia-like protrusion on the surface of HC-like cells differentiated from MERRF-iPSCs. ***, p<0.001, N=3.

FIG. 6A shows schematic of the HC differentiation protocol with lentiviral infections (MYO7A$^{mCherry}$ reporter gene, ATOH1, RFX1/RFX3, and ATOH1/RFX1/RFX3) on Day 21. FIG. 6B shows the number of MYO7A$^{mCherry}$-positive cells in the ATOH1/RFX1/RFX3, and the ATOH1 condition was higher than that in the control (Ctrl) condition. The number of MYO7$^{mCherry}$-positive cells in the ATOH1/RFX1/RFX3 and ATOH1 conditions was higher than those in the RFX1/RFX3 and ATOH1 conditions. Positive cells were counted by randomly selecting five fields in each experimental condition. Data are presented as mean±SD, , p<0.01, *, p<0.001. FIGS. 6C and 6D demonstrate that HC-like cells acquired numerous cilia on the cell surfaces in the ATOH1 condition, mostly acquired through clustered cilia in the RFX1/RFX3 condition, and more mature stereociliary bundles were acquired in the ATOH1/RFX1/RFX3 condition. Scale bar=2.5 μm in the control (Ctrl), ATOH1, and RFX1/RFX3, and 1.5 μm in ATOH1/RFX1/RFX3. FIG. 6E shows the number of clustered cilia in an area of 100 μm$^2$ measured in ten fields of the SEM image. Data are presented as mean±SD, *, p<0.001. FIG. 6F shows the stereocilium length measured from the cilia in ten fields of the SEM image using ImageJ software. The average stereocilium lengths of HC-like cells in the Ctrl, ATOH1, RFX1/RFX3, and ATOH1/RFX1/RFX3 conditions were 3.52±0.29 μm, 3.41±0.24 μm, and 3.05±0.23 μm, respectively. Data are presented as mean±SD. FIG. 6G** shows the immunofluorescent staining for the expression of ESPN and MYO7A in the iPSC-differentiated HCs by ATOH1, RFX1/RFX3, and ATOH1/RFX1/RFX3.

FIG. 8A demonstrates that through ATOH1/RFX1/RFX3 TF-driven HC differentiation, M1$^{ctrl}$-HC-like cells acquired more mature stereociliary bundles than M1 and M2 HC-like cells. Scale bar=2.5 μm. FIG. 8B shows the number of stereociliary bundle-like protrusions in a field measured in four different fields of the SEM image. Data are presented as mean±SD. N=3, *, p<0.05.

DETAILED DESCRIPTION OF THE EMBODIMENTS

Figure 1A:
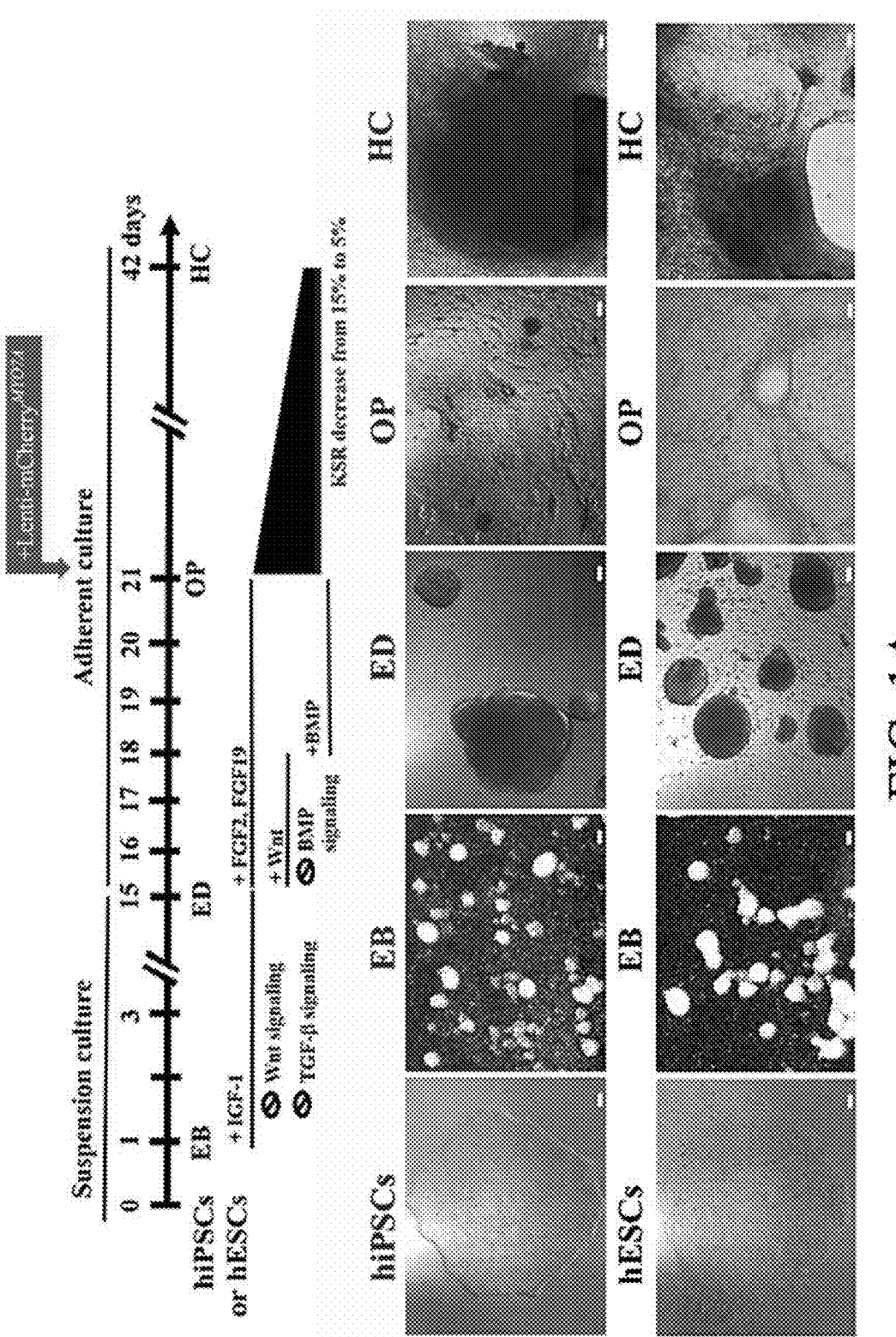
FIGS. 1A and 1B show the morphological and mRNA expression analyses during hair cell (HC) differentiation from human iPSCs (hiPSCs) or human ESCs (hESCs) through a non-TF method.

The following specific examples are used for illustrating the present disclosure. A person skilled in the art can easily conceive the other advantages and effects of the present disclosure. The present disclosure can also be implemented by different specific cases enacted or applications, and the details of the instructions can also be based on different perspectives and applications in various modifications and changes that do not depart from the spirit of the disclosure.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Provided is a method for treating hearing loss in a subject in need thereof, comprising providing a set of nucleic acids or a set of polypeptides for inducing generation of a mature HC-like cell, thereby treating the hearing loss in the subject, wherein the set of nucleic acids comprises a first nucleic acid encoding ATOH1, a second nucleic acid encoding RFX1, and a third nucleic acid encoding RFX3, and wherein the set of polypeptides comprises ATOH1, RFX1, and RFX3.

As used herein, the RFX gene family has seven members in mammals (RFX1 to RFX7). RFX1 is a negative regulator of human FGF1 gene activation, whereas RFX2 is a positive regulator of human FGF1 gene activation. Further, RFX1, RFX2, and RFX3 can regulate ALMS1, which encodes a centrosomal protein and is required for the proper function of primary cilia. (12)

In an embodiment of the present disclosure, the generation of the mature HC-like cell is driven by differentiation of an otic progenitor cell, or by direct reprogramming from a somatic cell of the subject.

In the method of the present disclosure, the differentiation of HC-like cells from the otic progenitor cell can be induced in the presence of transcription factors ATOH1/RFX1/RFX3 in vitro or in vivo and the differentiation is efficient and results in more mature HC-like cells.

In an embodiment of the present disclosure, the otic progenitor cell can be in the inner ear of the subject.

In an embodiment of the present disclosure, the otic progenitor cell can be differentiated from an iPSC. In another embodiment of the present disclosure, the method further comprises obtaining a somatic cell from the subject for producing the iPSC or producing the otic progenitor cell or the HC-like cell by direct reprogramming. In yet another embodiment of the present disclosure, the examples of the somatic cell include, but not limited to, a fibroblast, a keratinocyte, a peripheral blood cell and an epithelial cell. In an embodiment of the present disclosure, the iPSC is derived from a subject suffering from hearing loss involving degeneration or loss of inner ear hair cells. In another embodiment of the present disclosure, the subject suffers from sensorineural hearing loss. In yet another embodiment of the present disclosure, the subject has myoclonus epilepsy associated with ragged-red fibres syndrome, and the hiPSC is derived from the somatic cell with mtDNA A8344G point mutation. In an embodiment of the present disclosure, the method further comprises providing the abovementioned set of nucleic acids or the abovementioned set of polypeptides for the somatic cell from the subject.

In an embodiment of the present disclosure, the direct reprogramming from a somatic cell can be induced in the presence of transcription factors ATOH1/RFX1/RFX3. In another embodiment of the present disclosure, an additional transcription factor, such as Pou4F3 and GFi1, may also be included in the direct reprogramming from the somatic cell.

In an embodiment of the present disclosure, the transcription factors ATOH1/RFX1/RFX3 can be provided to the otic progenitor cell or the somatic cell by directly delivering the polypeptides of ATOH1, RFX1, and RFX3 to the otic progenitor cell or the somatic cell.

In an embodiment of the present disclosure, the transcription factors ATOH1/RFX1/RFX3 can be provided to the otic progenitor cell or the somatic cell by the use of expression vector(s). The expression vector(s) comprises the nucleic acids encoding ATOH1, RFX1, and/or RFX3, and allows production of transcription factors ATOH1/RFX1/RFX3 in the otic progenitor cell. The examples of the expression vector used in the method of the present disclosure include, but not limited to, a eukaryotic expression vector, a lentivirus vector, an adenoviral vector, a retroviral vector, an adeno-associated virus (AAV) vector and a Sendai viral vector.

In an embodiment of the present disclosure, the mature hair cell-like cell derived from the iPSC or the somatic cell can serve as a disease modelling system. In another embodiment of the present disclosure, the method provides a disease modelling system, which can be used as a drug screening platform designed to identify drugs that favorably treat hearing loss.

The present disclosure further provides a method of generating an inner ear cell from a pluripotent stem cell, comprising differentiating the pluripotent stem cell into an otic progenitor cell; and culturing the otic progenitor cell in the presence of a set of nucleic acids or a set of polypeptides to obtain a population comprising the inner ear cell, wherein the set of nucleic acids comprises a first nucleic acid encoding ATOH1, a second nucleic acid encoding RFX1, and a third nucleic acid encoding RFX3, and wherein the set of polypeptides comprises ATOH1, RFX1, and RFX3. In an embodiment of the present disclosure, the otic progenitor cell is cultured in the absence of a feeder cell to obtain the inner ear cell.

In an embodiment of the present disclosure, the pluripotent stem cell may be hiPSC. In an embodiment of the present disclosure, the hiPSCs are differentiated using the otic guidance protocol by: first, generating embryoid bodies (EBs) in suspension from hiPSCs; and then, subjecting the EBs into the formation of ectoderm. Then, the ectoderm undergoes an otic induction phase in an adherent cell culture to form OPs, which then independently differentiate into the surrounding tissues including HCs.

In another embodiment of the present disclosure, reverse transcription polymerase chain reaction (RT-PCR) analysis is used to characterize the properties of the cells at different stages, and also to investigate the expression of the upregulated transcription during the differentiation process. In an embodiment of the present disclosure, sensory inner ear HC markers, such as MYO7A and ESPN, are upregulated after long-term HC differentiation, indicating that differentiated cells derived from iPSCs in the inner ear HC induction system adopt a phenotype of HC-like cells. In another embodiment of the present disclosure, mRNA expression of RFX1 and RFX3 is also detected in the ectodermal differentiation (ED)/HC, ED, and ED/OP/HC stages, respectively, implying that RFX1 and RFX3 may play regulatory roles in the differentiation of HC-like cells, but not RFX2.

In an embodiment of the present disclosure, lentivirus carrying an MYO7A promoter as a reporter gene is used to infect cells at the OP stage and express mCherry, a red fluorescent protein in the cell with MYO7A expression for viewing with fluorescent microscopy.

In another embodiment of the present disclosure, morphology of the stereociliary bundle or hair bundle on the surface of HC-like cells induced with a non-TF method was observed through SEM imaging, and it was found out that they did not closely resemble the typical morphology of the mechanosensory stereociliary bundles of inner ear HCs. The lack of typical stereociliary bundle morphology of the non-TF induced HC-like cells indicates their status at the nascent state of development and failure to completely mature in an in vitro culture system.

In an embodiment of the present disclosure, ATOH1/RFX1/RFX3 efficiently promotes the differentiation of iPSCs into mCherry$^{MYO7A}$(+) cells more than ATOH1 alone or RFX1/RFX3 alone, suggesting that RFX1/RFX3 alone or ATOH1 alone is insufficient to promote effective inner ear HC differentiation.

In another embodiment of the present disclosure, the cilium morphology of HC-like cells in the ATOH1/RFX1/RFX3 condition exhibits stereociliary bundle-like protrusions, as compared to tightly squeezed cilia on the cell surface of HC-like cells in the ATOH1, and clustered but splayed cilia found in the RFX1/RFX3 condition. In an embodiment of the present disclosure, the expressions of classic HC marker genes MYO7A and ESPN in the ATOH1/RFX1/RFX3 conditions are significantly higher than those in the ATOH1 condition. The expression levels of MYO7A and ESPN in the RFX1/RFX3 condition are similar to those in the Ctrl condition. RFX1/RFX3 induces upregulated HC marker gene expression levels only when being in combination with ATOH1.

In an embodiment of the present disclosure, iPSCs can be derived from deaf patients with deafness gene mutations, including nuclear gene mutations and mitochondrial DNA mutations. For example, iPSCs from MERRF patients are obtained for characterizing the iPSCs and differentiation process in the presence of mtDNA A8344G mutation.

In another embodiment of the present disclosure, the disease modelling of MERRF syndrome is carried out by inducing the iPSCs differentiation by the method of the present disclosure.

The present disclosure further provides a kit for treating hearing loss, comprising a set of expression vectors including a first expression vector having a first nucleic acid encoding ATOH1; a second expression vector having a second nucleic acid encoding RFX1; and a third expression vector having a third nucleic acid encoding RFX3, wherein the set of expression vectors allows production of transcription factors comprising ATOH1, RFX1, and RFX3 in a host cell.

In an embodiment of the present disclosure, at least one of the first, second and third expression vectors is a lentiviral vector. In another embodiment of the present disclosure, the host cell is an otic progenitor cell derived from a human iPSC.

Many examples have been used to illustrate the present disclosure. The examples below should not be taken as a limit to the scope of the disclosure.

EXAMPLES

Human iPSCs hiPSCs were generated from human fibroblasts derived from the patients with MERRF syndrome (mtDNA A8344G point mutation). The patients with MERRF syndrome were a 15-year-old Chinese girl (M1) and her 13-year-old sister (M2). MERRF-iPSCs (M1- and M2-iPSCs) were reprogrammed by using four TFs, i.e., SOX2, OCT4, KLF4, and GLIS1, with retroviral vectors and were generously provided by Prof. Shih-Hwa Chiou at Taipei Veterans General Hospital, Taiwan. hiPSCs were cultured on Geltrex (Life Technologies)-coated dishes in the mTeSR$^{TM}$1 medium (Stemcell Technologies). M1$^{ctrl}$-iPSCs, which are isogenic iPSCs without A8344G mutation of mtDNA, were also prepared by heteroplasmy during iPSC reprograming. The pluripotency of M1$^{ctrl}$-iPSCs, M1-iPSCs, and M2-iPSCs was demonstrated by the expression of pluripotent markers, such as OCT4 and Nanog. The ability of M1$^{ctrl}$-iPSCs, M1-iPSCs, and M2-iPSCs to differentiate into three germ layers in vitro and form teratoma and three germ layers in vivo was also confirmed.

Embryoid Body (EB) Formation

For EB formation, hiPSCs or hESCs were dissociated with dispase (Stemcell Technologies) and transferred to ultralow attachment surface plates (Corning) containing the mTeSR™1 medium. EBs were cultured in ultralow attachment surface plates containing the mTeSR™1 medium supplemented with 100 ng/mL of recombinant human DKK-1 (R&D Systems), 3 mM of SIS3 (Sigma), and 10 ng/mL of IGF1 (Sigma) for 15 days.

Induction of Otic Progenitors (OPs)

For OP induction, the EBs were transferred into a poly-L-ornithine (Sigma) and laminin (Sigma)-coated plate and cultured for 3 days in an advanced Dulbecco's Modified Eagle Medium/Nutrient Mixture F12 (DMEM/F12) supplemented with 20% knockout serum replacement (KSR), N2, B27 (ThermoFisher Scientific, USA), human bFGF (25 ng/mL; R&D Systems), human FGF19 (25 ng/mL; R&D Systems), human Noggin (30 ng/mL; R&D Systems), human R-spondin 1 (50 ng/mL; R&D Systems), heparan sulphate (50 ng/mL; Sigma), and ampicillin (50 μg/mL). Then, the medium was replaced with the advanced DMEM/F12 supplemented with 15% KSR, N2, and B27, human bFGF (25 ng/mL), human FGF19 (25 ng/mL), human BMP4 (20 ng/mL; R&D Systems), heparan sulphate (50 ng/mL), and ampicillin (50 μg/mL) and cultured for 3 days.

Inner Ear HC-Like Cells Differentiation

For inner ear HC-like cells differentiation, the medium was replaced with the advanced DMEM/F12 supplemented with 15% KSR, N2, and B27, and ampicillin (50 mg/mL). The concentration of KSR progressively decreased until day 42. The lentivirus vector pEZX-LvPM02 (Genecopoeia) that carries the MYO7A promoter-driven mCherry gene as a reporter gene was used to infect differentiated cells on day 21 OPC stage for monitoring the following HC differentiation.

Production of viruses

Lentiviral vectors lenti-RFX1 and lenti-RFX3 were constructed from the pSG5-RFX1 and pSG5-RFX3 constructs provided by Dr. Shaul and Dr. Iwama. (13, 14) Lenti-ATOH1 vector was purchased from Genecopoeia. Lenti-ATOH1, lenti-RFX1, lenti-RFX3 and lenti-mCherry$^{MYO7A}$ vectors were transfected into HEK293T cells. After 48 hr, viruses were harvested. Viral supernatants were concentrated using an ultracentrifuge for 2 h at 100,000×g. Global UltraRapid Lentiviral Titer Kit (System Biosciences) was used to determine viral titers.

Reverse Transcription Polymerase Chain Reaction (RT-PCR)

Total RNA was isolated using FavorPrep Tissue Total RNA Extraction Mini Kit (Favorgen, Ping-Tung, Taiwan).

10

Afterwards, Tri-Reagent RNA clean-up kit (Favorgen) was applied, and cDNA was synthesised using the iScript cDNA Synthesis kit (BIO-RAD). PCR was performed using the KAPA2G ReadyMix PCR kit (KAPABiosystems). The gene specific primer sequences are presented in Table 1 below.

RNA Isolation and Library Construction and Sequencing

The total RNA samples were first treated with DNase I to degrade any possible DNA contamination. Then, the mRNA was then enriched using the oligo (dT) magnetic beads and mixed with the fragmentation buffer to be fragmented into short fragments. Thereafter, the first strand of cDNA was synthesized using random hexamer primer. Buffer, dNTPs, RNase H and DNA polymerase I were added to synthesize the second strand. The double-strand cDNA was purified with magnetic beads. End repairation and 3'-end single nucleotide A (adenine) addition were then performed. Finally, sequencing adaptors were ligated to the fragments. The fragments were enriched through PCR amplification. During the quality control (QC) step, Agilent 2100 Bioanaylzer and ABI StepOnePlus Real-Time PCR System were used to qualify and quantify the sample library. The library products were then ready for sequencing by Illumina HiSeq™ 2000 or other sequencers.

Bioinformatic Analyses

Primary sequencing data produced by Illumina Nextseq™ 500, called raw reads, were subjected to QC to determine if a resequencing step is required. After QC, raw reads were filtered into clean reads for alignment to the reference sequences. A QC of the alignment was performed to determine if resequencing was required. The alignment data were utilized to calculate the distribution of reads on reference genes and the mapping ratio. If the alignment result passes the QC, it was further proceeded with the downstream analysis including gene expression and a deep analysis based on gene expression (e.g., PCA/correlation/screening DE genes). The bioinformatic analyses were performed by Genomic Inc. (New Taipei City, Taiwan).

Quantitative Polymerase Chain Reaction

Total RNA was isolated using the RNA clean-up kit (FavorPrep), and cDNA was synthesised using the cDNA synthesis kit (iScript) according to the manufacturer's instruction. PCR was performed using the KAPA SYBR FAST qPCR kit (KAPA Biosystems) and the 7900HT fast real-time PCR system. The gene specific primer sequence is presented in Table 1 below.

TABLE 1

| Primer sets for PCR and qPCR. | | | |
|---|---|---|---|
| Primer | Sequence | SEQ ID NO | Product Size (bp) |
| SOX2-F | 5'-TACAGCATGTCCTACTCGCAG-3' | 1 | 110 |
| SOX2-R | 5'-GAGGAAGAGGTAACCACAGGG-3' | | |
| OCT4-F | 5'-CTTCAGGCACTGTGTTCATTG-3' | 2 | 672 |
| OCT4-R | 5'-TTTGGCTGAACACCTTCCCA-3' | | |
| NANOG-F | 5'-AAGGTCCCGGTCAAGAAACAG-3' | 3 | 237 |
| NANOG-R | 5'-CTTCTGCGTCACACCATTGC-3' | | |

TABLE 1-continued

Primer sets for PCR and qPCR.

| Primer | Sequence | SEQ ID NO | Product Size (bp) |
|---|---|---|---|
| GATA6-F | 5'-CTCAGTTCCTACGCTTCGCAT-3' | 4 | 120 |
| GATA6-R | 5'-GTCGAGGTCAGTGAACAGCA-3' | | |
| Brach-yury-F | 5'-TATGAGCCTCGAATCCACATAGT-3' | 5 | 109 |
| Brach-yury-R | 5'-CCTCGTTCTGATAAGCAGTCAC-3' | | |
| SIX1-F | 5'-CTGCCGTCGTTTGGCTTTAC-3' | 6 | 135 |
| SIX1-R | 5'-GCTCTCGTTCTTGTGCAGGT-3' | | |
| EYA1-F | 5'-GTCACAGTCTCAGTCACCTGG-3' | 7 | 202 |
| EYA1-R | 5'-GGGATAAGACGGATAGTCCTGC-3' | | |
| PAX2-F | 5'-CGGCTGTGTCAGCAAAATCC-3' | 8 | 77 |
| PAX2-R | 5'-GCTTGGAGCCACCGATCA-3' | | |
| PAX6-F | 5'-TGGGCAGGTATTACGAGACTG-3' | 9 | 111 |
| PAX6-R | 5'-ACTCCCGCTTATACTGGGCTA-3' | | |
| DLX5-F | 5'-GTCTTCAGCTACCGATTCTGAC-3' | 10 | 89 |
| DLX5-R | 5'-CTTTGCCATAGGAAGCCGAG-3' | | |
| MYO7A-F | 5'-GCAGAACGCAACGCACATC-3' | 11 | 123 |
| MYO7A-R | 5'-TCCCGGTAGCGGATAAGCA-3' | | |
| RFX1-F | 5'-AGACCGGCGTTCCTACTCA-3' | 12 | 129 |
| RFX1-R | 5'-GCAGCGTAGTGGATAGGCAG-3' | | |
| RFX2-F | 5'-GCGATTGAAAACCTCCAAAA-3' | 13 | 290 |
| RFX2-R | 5'-GGCTTCAGACGAATCCCATA-3' | | |
| RFX3-F | 5'-AAACTGGACCCAGTCAATGC-3' | 14 | 197 |
| RFX3-R | 5'-TGTTGCATGGGTTGTTGTCT-3' | | |
| ESPN-F | 5'-CAGAGTGCAGGACAAAGACAA-3' | 15 | 153 |
| ESPN-R | 5'-GCAGCGTAGTGGATAGGCAG-3' | | |
| GAPDH-F | 5'-TGGTGGCAGTTACCTTACTACT-3' | 16 | 105 |
| GAPDH-R | 5'-CAAGGGCTCTTGATTTGCTGA-3' | | |

Immunofluorescent Staining

The cells were fixed with 4% paraformaldehyde for 15 min at room temperature. Nonspecific binding sites were blocked, and an additional permeabilisation step was performed for 1 h in 0.2% Triton X-100 and 1% bovine serum albumin. The cells were incubated overnight with a primary antibody at 4° C. Following this incubation, the fluorescein isothiocyanate- and tetramethylrhodamine-conjugated species secondary antibodies (1:500, Invitrogen, Carlsbad, Calif., USA) were used to detect the primary antibodies. The primary antibodies used in this study were anti-MyosinVIIa (1:500, Abcam, Cambridge, Mass., USA) and anti-Espin (1:500, Abcam, Cambridge, Mass., USA). Nuclei were visualised using the Hoechst stain (Invitrogen, Carlsbad, Calif., USA). For FM1-43 staining (Invitrogen, Carlsbad, Calif., USA), the cells were immersed in the stain solution on ice for 1 min according to the manufacturer's instructions. FM 1-43 staining was used to demonstrate that the iPSC-derived differentiated HC-like cells exhibit the expression of not only the HC markers (MYO7A and ESPN) but also specific ion channels in HCs. It was reported that FM 1-43 can be used to characterise HCs and examine the recycling of synaptic vesicle-associated activities.

Scanning Electron Microscopy (SEM)

The cells were fixed with 4% glutaraldehyde for 1 h, dehydrated in a graded ethanol series, and dried using critical point drying with liquid $CO_2$. Specimens were sputter coated with 100 A° Au/Pd and viewed using a Hitachi S-3500N variable pressure scanning electron microscope operated under a high vacuum of 5-10 kV.

Statistics Analyses

Data are expressed as means±SD. Independent t-test was used for comparison of two groups. One-way analysis of variance was used for comparison of multi-groups. The data were considered statistically significant at $p < 0.05$.

Example 1: Differentiation of Inner Ear HC-Like Cells from hiPSCs or hESCs Through a Non-TF Method hiPSCs were differentiated using the feeder cell-free otic guidance protocol, a non-TF method. (4) First, EBs were generated from hiPSCs or hESCs through a suspension cell culture with the addition of insulin growth factor-1 (IGF-1), which is an inhibitor of WNT and TGF-β signaling (FIG. 1A). Following EBs formation, the cells were maintained in conditions that suppressed the differentiation of endodermal and mesodermal lineages through the inhibition of the TGF-β and WNT signaling pathways so as to promote the formation of the cranial ectoderms, which has been reported on previous ectodermal guidance protocol in mouse ESCs. (3) The downregulation of WNT and TGF-β signaling can result in the formation of a primitive streak by the treatment of DKK-1 (Wnt inhibitor) and the selective inhibitor of Smad3 (SIS3, interference with TGF-β signaling), thus increasing the ectoderm differentiation (ED) during EB formation. IGF-1 and IGF signaling are suggested as being crucial for the differentiation of the cranial ectoderm; hence, the otic induction phase was initiated in an adherent cell culture after treatment of EBs with IGF-1, DKK-1, and SIS3.

After the generation of the presumptive cranial ectoderm and initiation of the otic induction phase in an adherent cell culture, EBs underwent a period of inductive FGF signaling, which involved an initial period of BMP inhibition with Noggin and WNT activation with R-spondin 1, followed by BMP4 treatment. These differentiated cells were a population of presumptive OPs. OPs independently differentiated into the surrounding tissues and did not require external signaling for correct differentiation; therefore, a protracted culture with a decreasing concentration of knockout serum replacement (KSR) was obtained for the differentiation of HC-like cells (FIG. 1A).

Figure 1B:
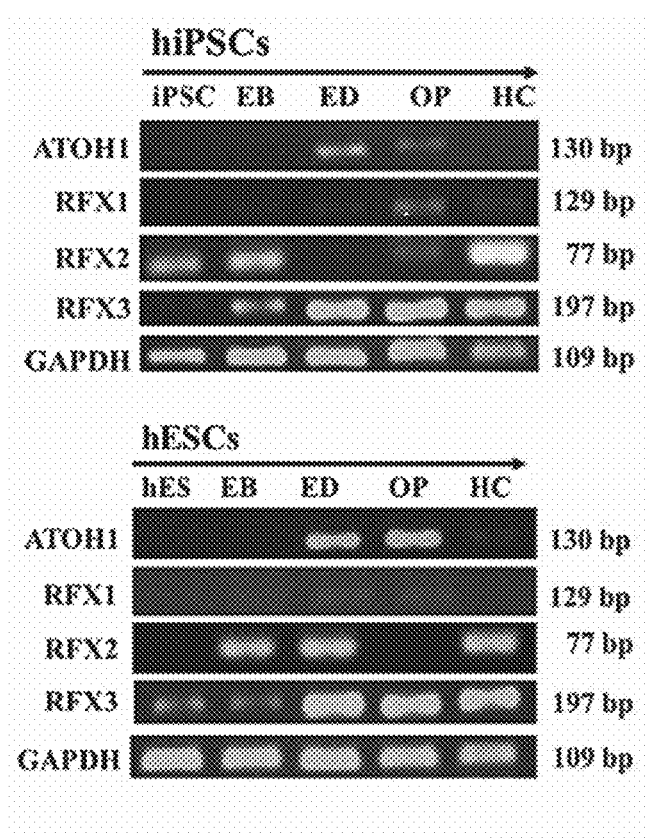

During the differentiation of hiPSCs or hESCs to HC-like cells, the mRNA expression levels of ATOH1, RFX1, RFX2, and RFX3 were analyzed through reverse transcription polymerase chain reaction (RT-PCR). It has been suggested that the expression of ATOH1 mRNA can be detected in otic progenitors (OP) and the early immature HC stage differentiated from hESCs (4), but not in HCs differentiated from mouse ESCs. (3) In the present disclosure, it was found that the mRNA expression of ATOH1 could be detected from the ectoderm differentiation (ED) to OP stages, but not at the late HC stage (Day 42) (FIG. 1B).

Furthermore, different mRNA expression patterns and levels of RFX1, RFX2, and RFX3 were detected at the HC stage after the differentiation of hiPSCs or hESCs for 42 days. Notably, the mRNA expression levels of RFX1 and RFX3 could be detected at the OP stage, but not RFX2, implying the crucial roles of RFX1 and RFX3 for inducing the OP into the HC stage by the non-TF method (FIG. 1B).

Figure 2A:
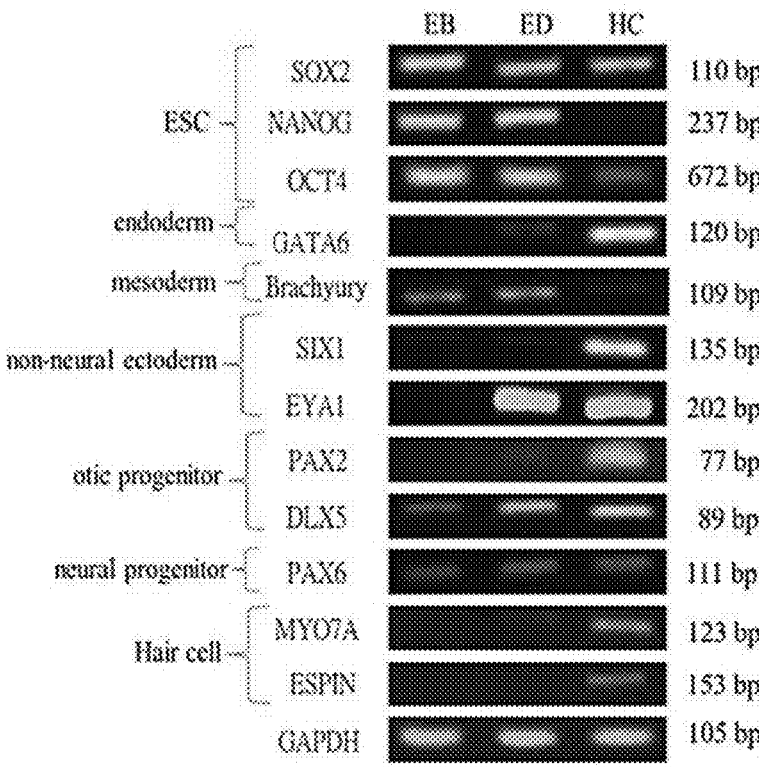
FIGS. 2A to 2C show expression patterns of HC markers in iPSC-differentiated HC-like cells through a non-TF method.

Example 2: Expression of HC Markers in iPSC-Differentiated HC-Like Cells Through a Non-TF Method SOX2, NANOG, and OCT4 were the important TFs for pluripotency and self-renewal of human ESCs, and SOX2 was a marker for the prosensory identity of otic lineage. (14-15) Reverse transcription polymerase chain reaction (RT-PCR) analyses revealed that the expression of pluripotency markers, SOX2, NANOG, and OCT4, was downregulated during the inner ear HC differentiation process; however, SOX2 was continuously expressed at the HC stage (FIG. 2A).

The expression of GATA6, the endodermal marker, and brachyury, the mesodermal marker, were not significantly upregulated during EB formation and the ED stage, indicating that the mesodermal and endodermal cells derived from hiPSC were suppressed by DKK-1 and SIS3. The expression of GATA6 was significantly upregulated at the HC stage, suggesting the existence of endoderm-derived cells at this stage. By contrast, brachyury, the mesodermal marker, was detected from the EB to ED stages, but not at the HC stage, while using the non-TF method. In addition, the expression of SIX1 and EYA1 were upregulated during the HC differentiation process, which are the marker genes demonstrated to be expressed in the preplacodal ectoderm; the formation of which is crucial for cranial development (FIG. 2A).

The transcriptional regulators PAX2 and DLX5 were markers of otic lineage, which have been reported in otic differentiation from human ESCs. The co-expression of these markers can serve as an indication of OP identity. DLX5 was detectable during EB formation through the ED and HC stages. The upregulation of PAX2 was also detected from the ED to HC stages (FIG. 2A).

Finally, sensory inner ear HC markers such as MYO7A and ESPN were upregulated after long-term HC differentiation, indicating that differentiated cells derived from iPSCs in the inner ear HC induction system adopt a phenotype of HC-like cells. Differentiated cells derived from iPSCs under this otic guidance condition also exhibited the expression of PAX6 (FIG. 2A).

The HC differentiation process of the hiPSCs can be monitored by following the expression of HC markers. Lentivirus carrying an MYO7A promoter fused with the mCherry reporter gene was used to infect cells at the OP stage and monitor the HC differentiation process of the hiPSCs or hESCs.

The lentiviral construct of MYO7A$^{mCherry}$ reporter used was purchased from GeneCopoeia™ (HPRM25722-PG02, GeneCopoeia, Rockville, Md., USA). The promoter details were as follows: >HPRM25722, NM 000260, NM 001127179; Entrez_ID=4647; chr11+:76837906-76839534; −1404 to +224, length=1629. It followed the method that Boeda et al. previously reported in the generation of human MYO7A promoter-GFP transgenic mice for targeting the MYO7A-positive cells in vivo. (18)

The expression of the GFP reporter gene was under the control of the human MYO7A promoter region −2109 to +2370. Notably, the promoter region (−1404 to +224) of the MYO7A$_{mcherrY}$ reporter gene used in this study was within the MYO7A promoter (−2109 to +2370) in MYO7A promoter-GFP transgenic mice. These GFP transgenic mice were found to have the following characteristics: (1) GFP expression was specifically restricted to HCs in the inner ear and cochlear; and (2) GFP expression was not observed in other organs.

Figure 2B:
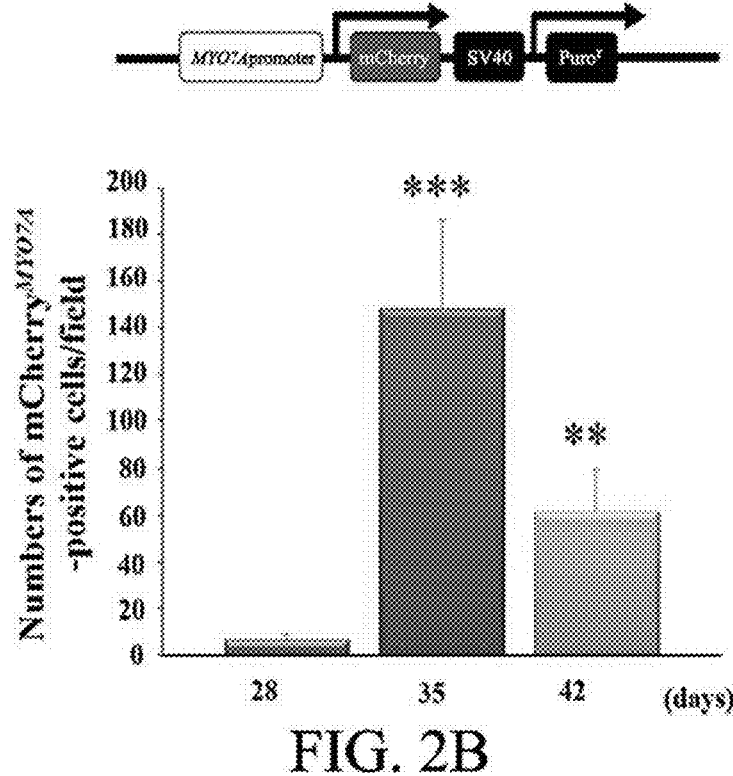

The differentiated cells at the OP stage were infected with lenti-MYO7A$^{mCherry}$ virus on Day 21 (FIGS. 1A and 2B). The numbers of MYO7A$^{mCherry}$-positive cells were semi-quantitatively counted by selecting five different fields under a florescent microscope in which the mCherry-positive cells were counted. After infecting the OPs with the lenti-MYO7A$^{mCherry}$ virus on Day 21, the number of MYO7A$^{mCherry}$-positive cells was significantly higher on Days 35 and 42 than that on Day 28 (FIG. 2B).

Consistently, the number of MYO7A$^{mCherry}$-positive cells was positively correlated with the mRNA expression of MYO7A in the HC stage at Day 42 after differentiation (FIGS. 2A and 2B).

Figure 2C:
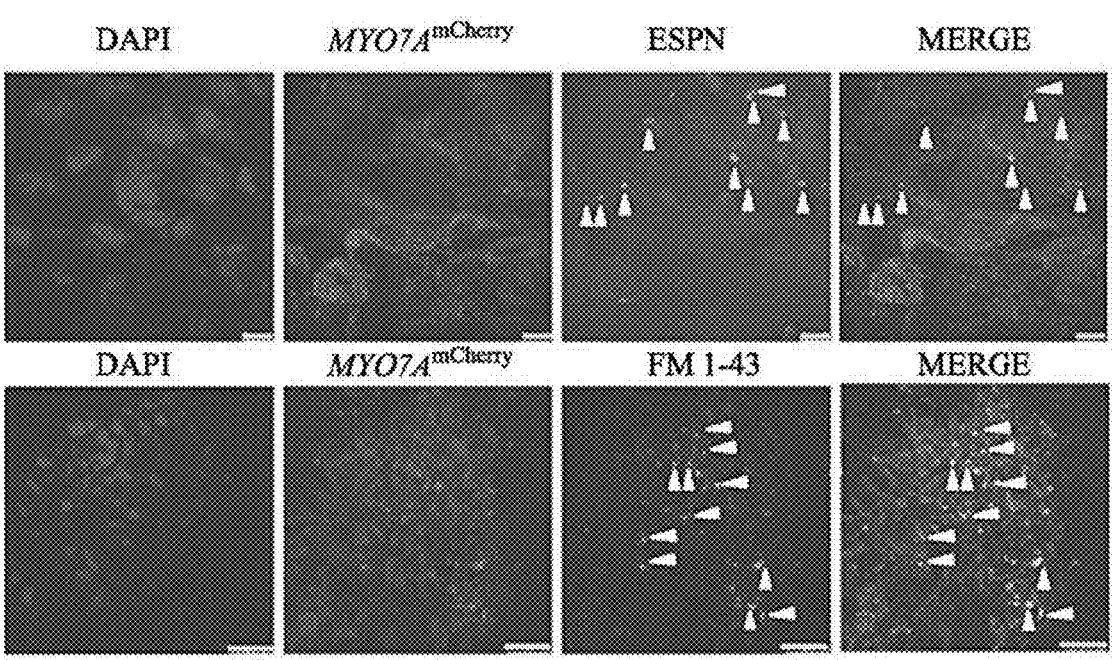

Immunofluorescence staining was further used to demonstrate that MYO7A$^{mCherry}$-positive cells were colocalised with the staining signal of mature HC markers ESPN and FM 1-43 (FIG. 2C). ESPN has been suggested as a critical structural marker for the actin filament cross-link in stereociliary bundles, and FM 1-43 fluorescent dye rapidly and specifically labels inner ear HCs by permeating the mechanotransduction channels. Notably, the mRNA expression levels of sensory inner ear HC markers such as MYO7A and ESPN were upregulated after long-term HC differentiation, indicating that the formation of HC-like cells occurred (FIG. 2A).

Figure 3:
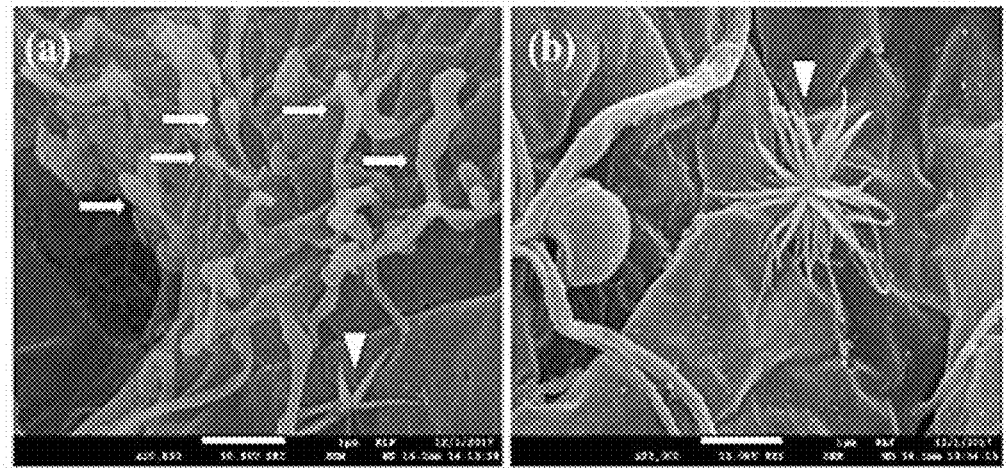
FIG. 3 shows the morphology of cilia on the surface of HC-like cells, as determined through scanning electron microscope (SEM), wherein the HC-like cells is differentiated from hiPSCs through a non-TF method. The arrow indicates the single cilium, and the arrowhead indicates the clustered cilia. Scale bar=1 μm.

Example 3: Differentiated HC-Like Cells Failed to Acquire Mature Stereociliary Bundles Through a Non-TF Method The morphology of the stereociliary bundle or hair bundle on the surface of HC-like cells was analysed with scanning electron microscopy (SEM) imaging. In epithelium-like areas, cilium-like protrusions extended from the surface of cells. In most cases, these protrusions displayed a single cilium (arrow in FIG. 3) or a cluster of cilia (arrowhead in FIG. 3); however, the clustered cilia were splayed and did not closely resemble the typical morphology of the mechanosensory stereociliary bundles of inner ear HCs.

The lack of typical stereociliary bundle morphology suggested the nascent state of development of these HC-like cells and may fail to completely mature in an in vitro culture system. The HC-like cells did not exhibit a typical mature physiological morphology most likely due to the absence of environmental cues.

Example 4: Differentiation of HC-Like Cells from iPSCs of Patients with MERRF Syndrome Through a Non-TF Method Myoclonus epilepsy associated with ragged-red fibres (MERRF) syndrome is characterised by mtDNA A8344G mutation, resulting in impairment of the synthesis of mitochondrial proteins that are important for oxidative phosphorylation.

Figure 4A:
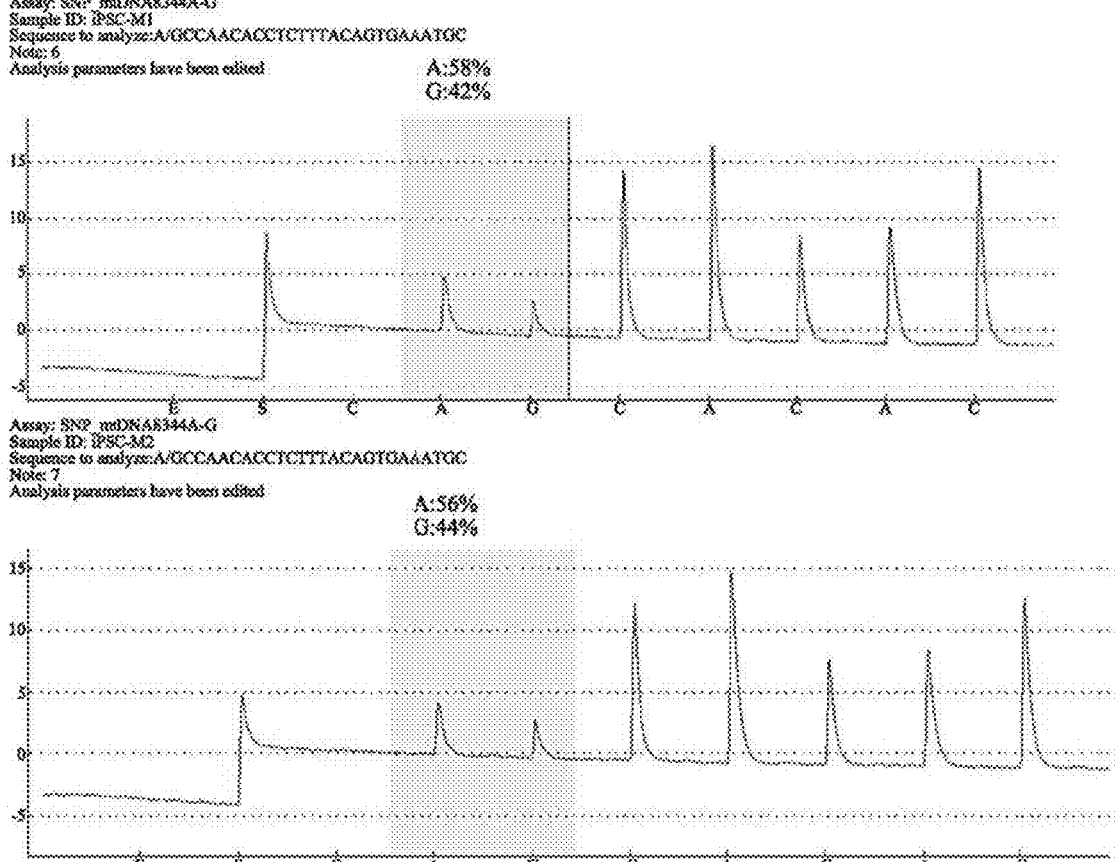
FIGS. 4A to 4C show characterisation of the hiPSCs harbouring the A8344G mutation of mtDNA.

The mutation load of mtDNA A8344G in MERRF fibroblast-derived iPSCs were determined using a pyrosequencing assay conducted at the beginning of otic guidance differentiation. Quantitative analysis revealed mutation rates of approximately 42.05% in M1-iPSCs and 44.23% in M2-iPSCs (FIG. 4A and Table 2).

TABLE 2

| Quantitative analysis of mutation rates | | | |
|---|---|---|---|
| | | Frequency (%) | |
| Assay | Sample ID | A | G |
| mtDNA 8344A/G | M1-iPSCs | 57.95 | 42.05 |
| mtDNA 8344A/G | M2-iPSCs | 55.77 | 44.23 |

Figure 5A:
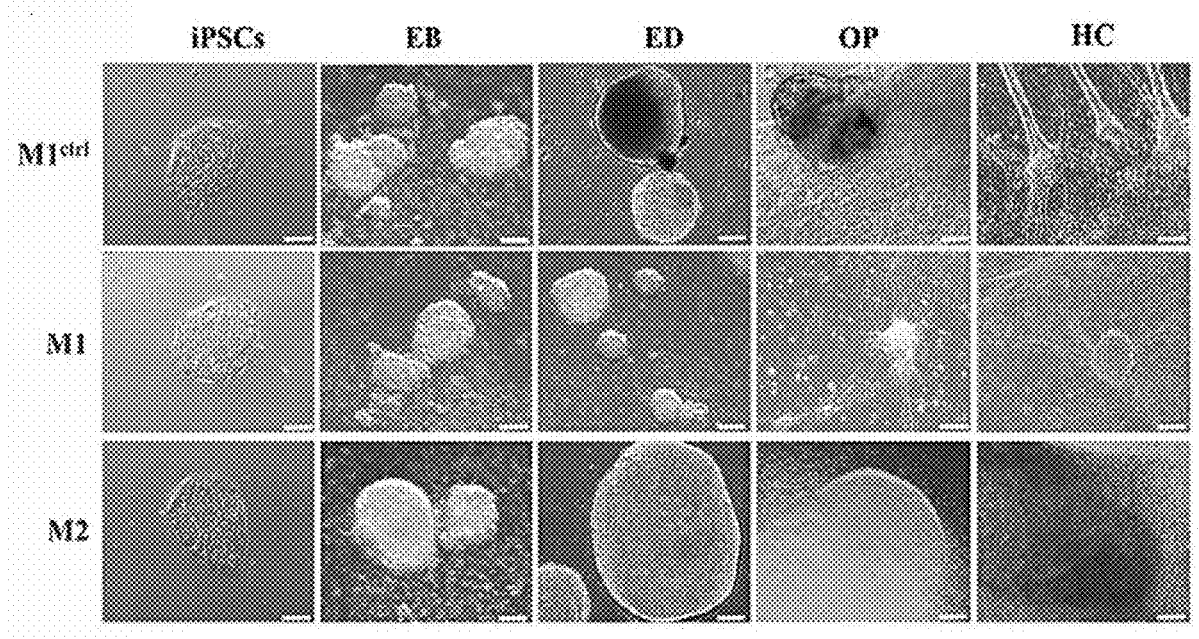
FIGS. 5A to 5I show characterisation of the HC-like cells differentiated from the hiPSCs harbouring the A8344G mutation of mtDNA through a non-TF method.
Figure 5B:
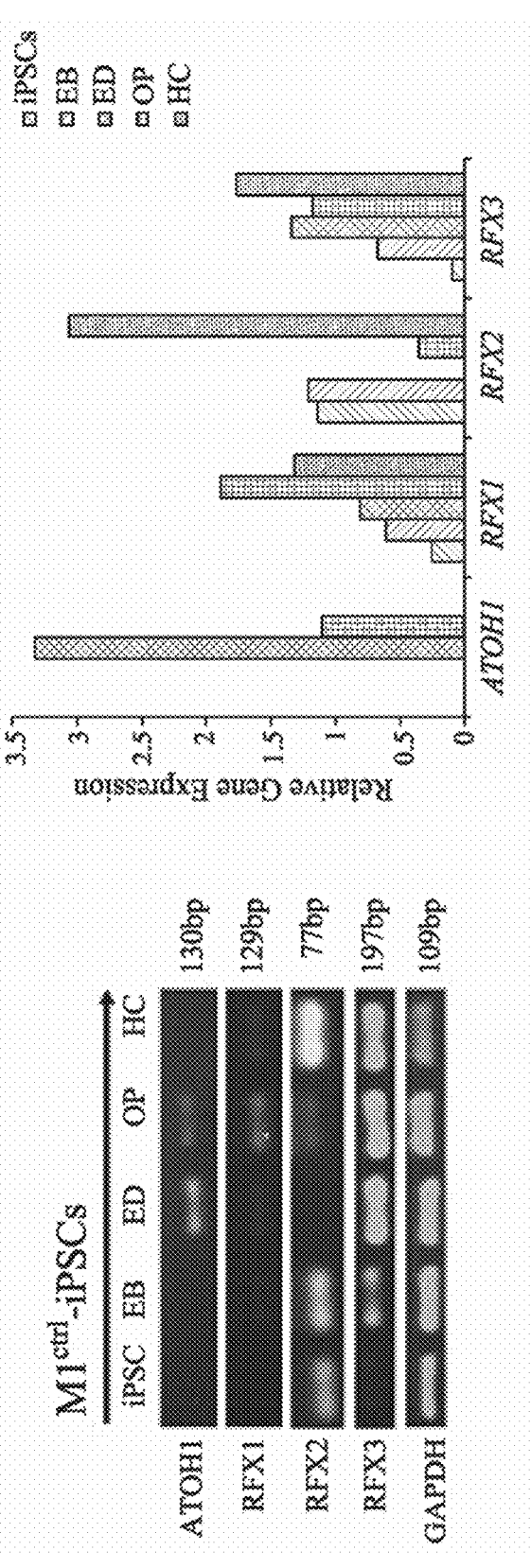
Figure 5C:
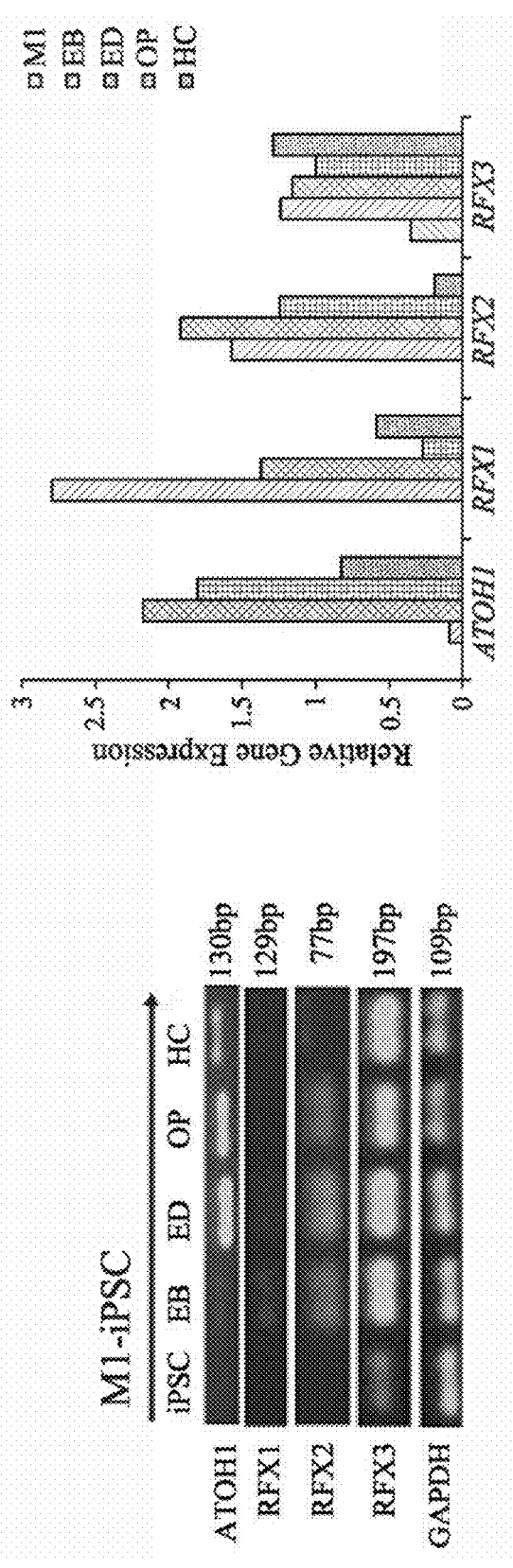
Figure 5D:
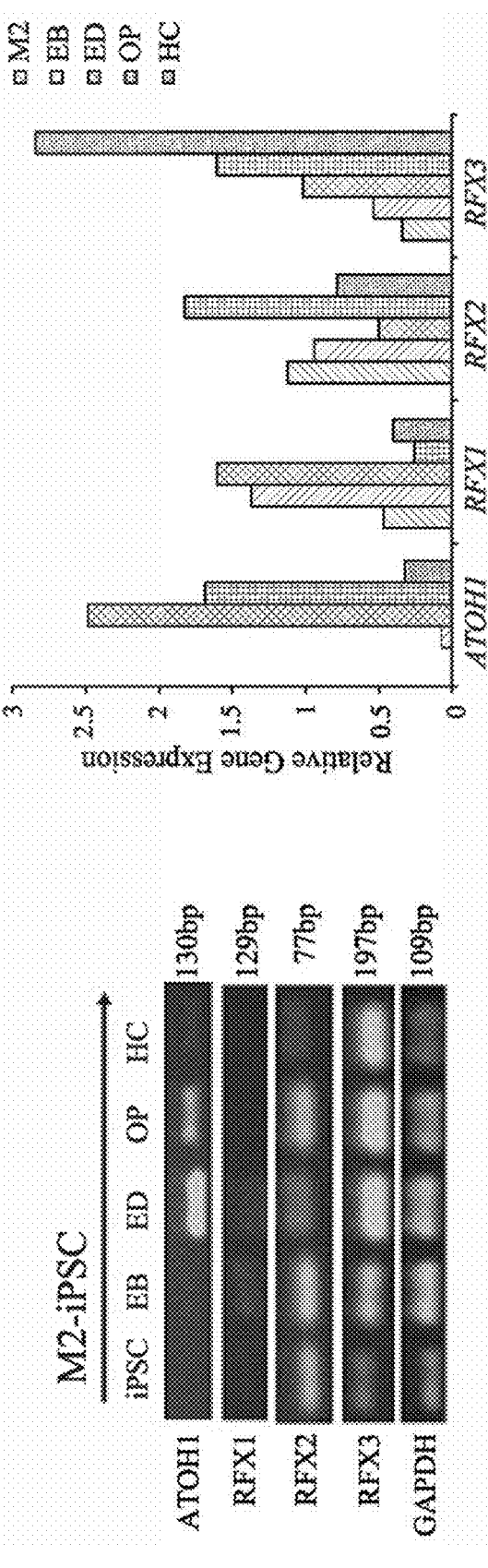

It was observed that the A8344G mutation of mtDNA did not affect the morphology of M1-iPSC and M2-iPSC colonies during iPSC culturing (FIG. 5A). M1$^{ctrl}$-iPSCs are isogenic iPSCs without A8344G mutation of mtDNA due to heteroplasmy during iPSC reprograming In addition, it is noteworthy that the mRNA expression levels of ATOH1, RFX2, and RFX3 could be detected at the ED, OP, and HC stages after the differentiation of M1 and M2-iPSCs (FIGS. 5C and 5D). Notably, the mRNA expression level of RFX1 was reduced in the OP and HC stages after the differentiation of M1 and M2-iPSCs (FIGS. 5C and 5D). By contrast, the mRNA expression of RFX1 was observed in the OP and HC stages after the differentiation of hESCs and M1$^{ctrl}$-iPSCs (FIGS. 1B and 5B), suggesting that the downregulation of mRNA expression of RFX1 in M1-HCs and M2-HCs might also account for the defects in the stereociliary bundles of M1-HCs and M2-HCs.

Figure 4B:
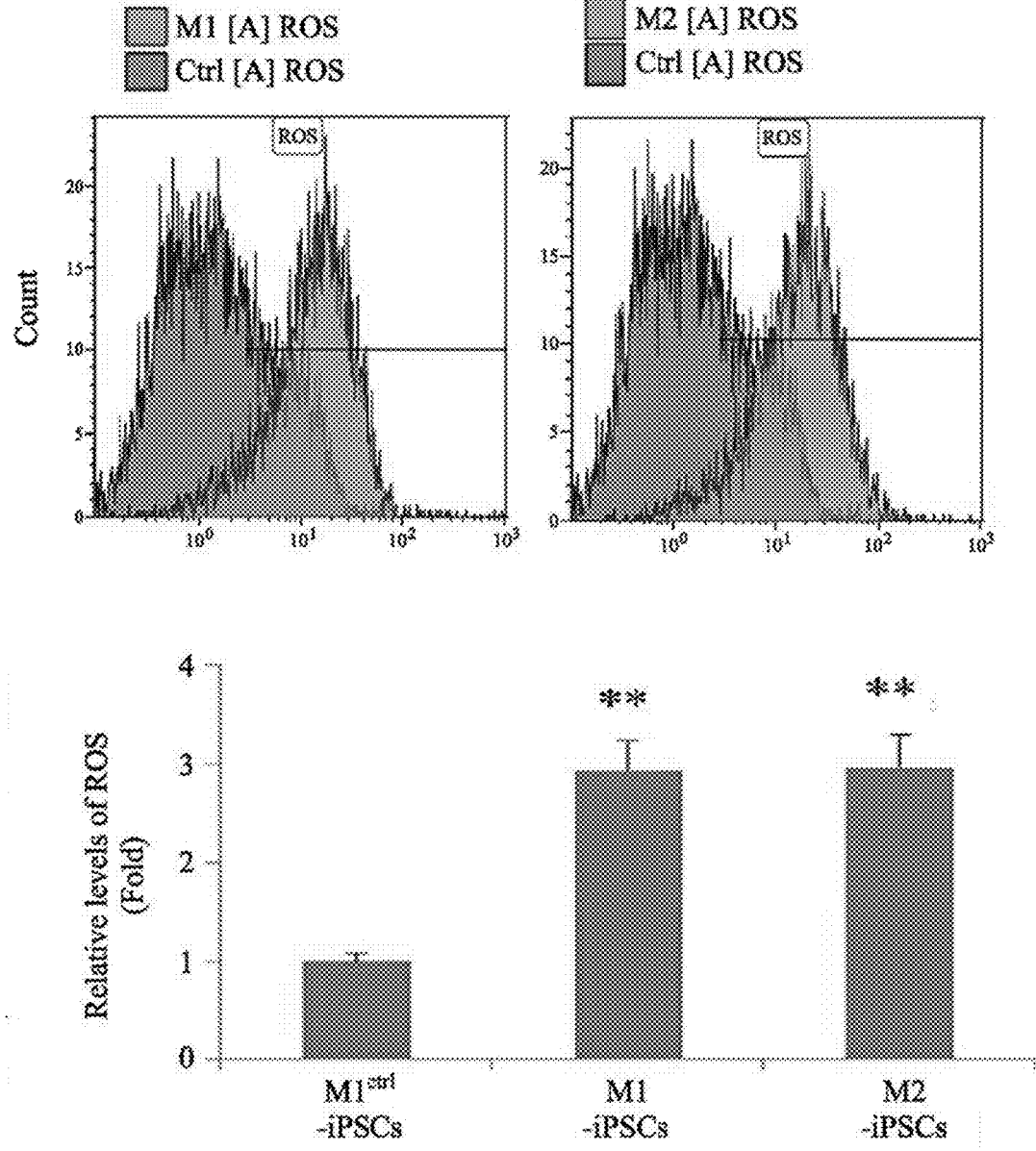

Example 5: mtDNA A8344G Mutation Causes Reactive Oxygen Species (ROS) Accumulation and Alters Antioxidant Gene Expression in iPSCs and iPSC-Derived Inner Ear HCs The dysfunction of mitochondria may cause endogenously elevated ROS levels and alter the expression of antioxidant genes in cells. In previous studies, the mtDNA mutation elicited oxidative damage, and altered gene expression in patients with MERRF syndrome. (4) To determine the ROS levels in iPSCs and HC-like cells derived from iPSC, iPSCs and HC-like cells were stained with CellROX, a green fluorescent dye, for the detection of ROS in living cells. The intracellular ROS levels in M1-iPSCs and M2-iPSCs were significantly three times higher than those in M1$^{ctrl}$-iPSCs (FIG. 4B).

Figure 5E:
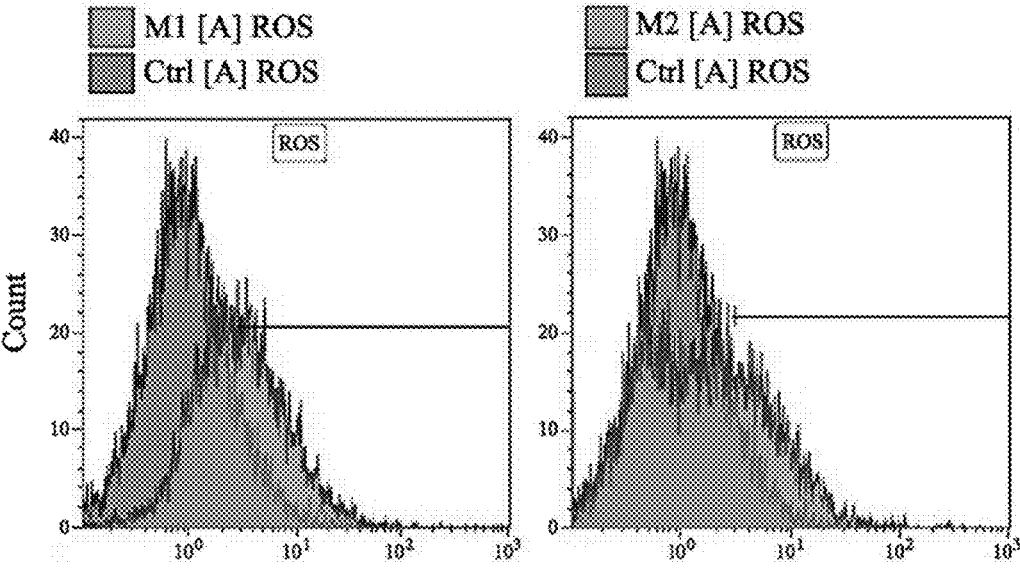
Figure 5E:
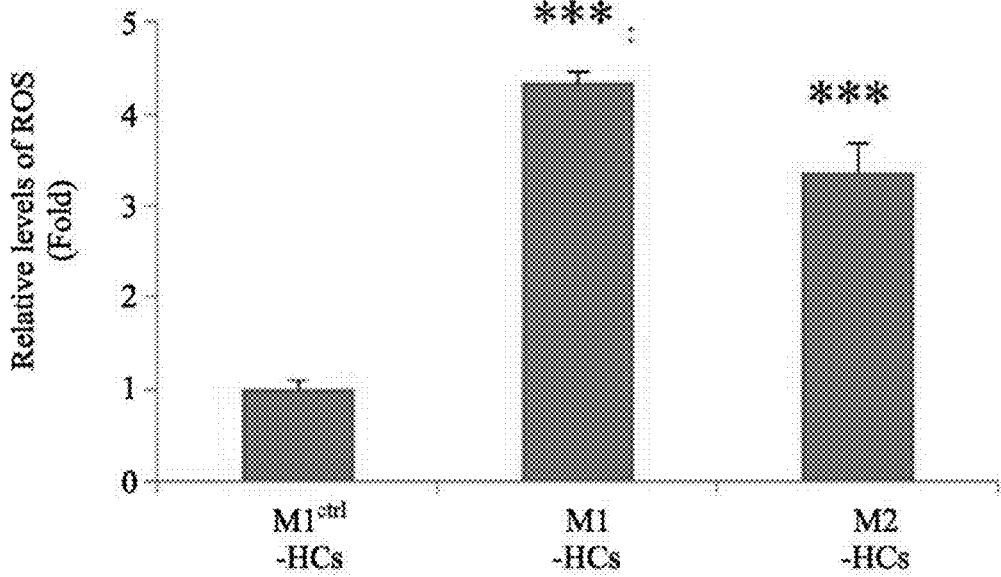

After otic guidance differentiation by the non-TF method, the intracellular ROS levels in M1-HC-like cells and M2-HC-like cells were significantly higher than those in M1$^{ctrl}$-HC-like cells (FIG. 5E).

Figure 4C:
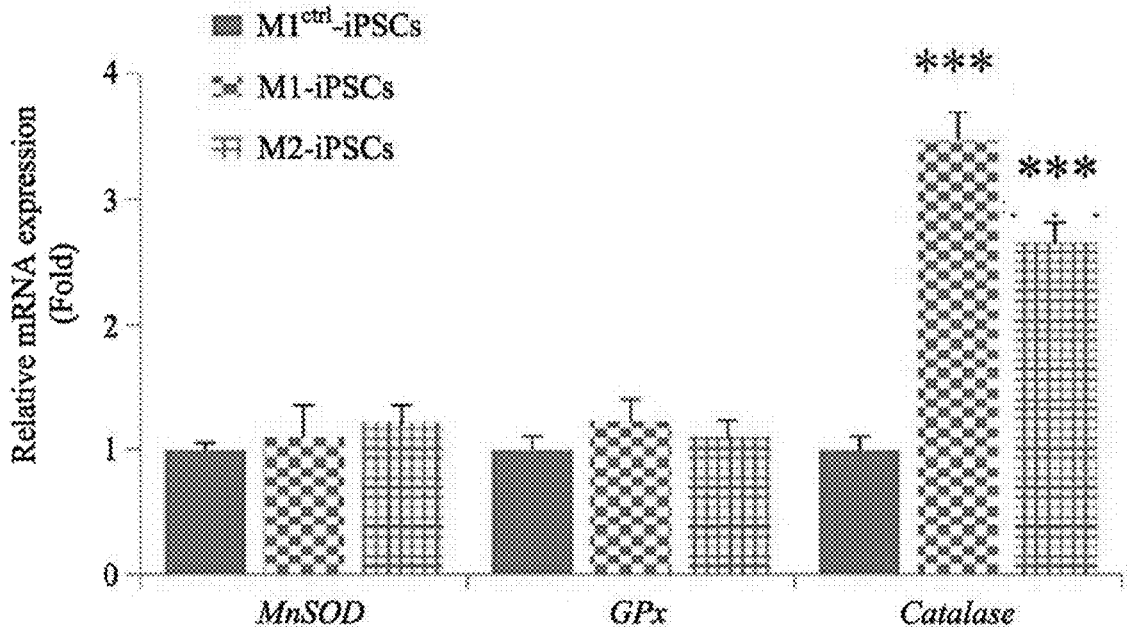

Furthermore, the expression of antioxidant genes including MnSOD, GPx, and CAT was analysed by quantitative RT-PCR. The results revealed significantly upregulated catalase expression in M1-iPSCs and M2-iPSCs; however, their expression levels of MnSOD and GPx remained similar to those in M1$^{ctrl}$-iPSCs, indicating the impaired hydrogen peroxide and hydroxyl radical scavenging capacities of MERRF-iPSCs (FIG. 4C).

Figure 5F:
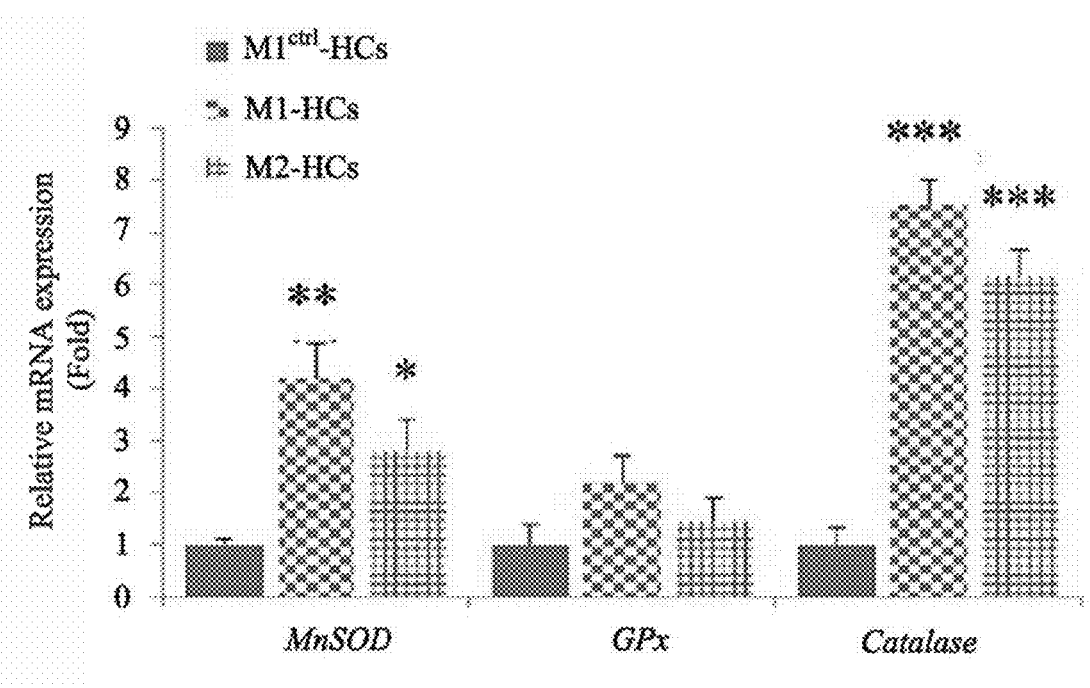

After otic guidance differentiation by the non-TF method, significant upregulated expression of MnSOD and CAT were observed in the M1- and M2-HC-like cells; however, the expression level of GPx in these cells remained similar to that in M1$^{ctrl}$-HC-like cells, indicating the impaired hydroxyl radical scavenging capacity of the MERRF-HC-like cells (FIG. 5F). Collectively, elevated ROS levels and impaired ROS scavenging capacities in the MERRF-iPSCs and the differentiated progenies MERRF-HC-like cells were observed.

These changes such as the elevation of ROS levels and impaired antioxidant CAT expression in M1$^{ctrl}$-iPSCs, M1-iPSCs, M2-iPSCs and M1$^{ctrl}$-HCs/M1-HCs/M2-HCs were similar to the previous findings in cardiomyocytes and NPCs differentiated from M1$^{'1}$-iPSCs, M1-iPSCs, and M2-iPSCs. (11)

Figure 6A:
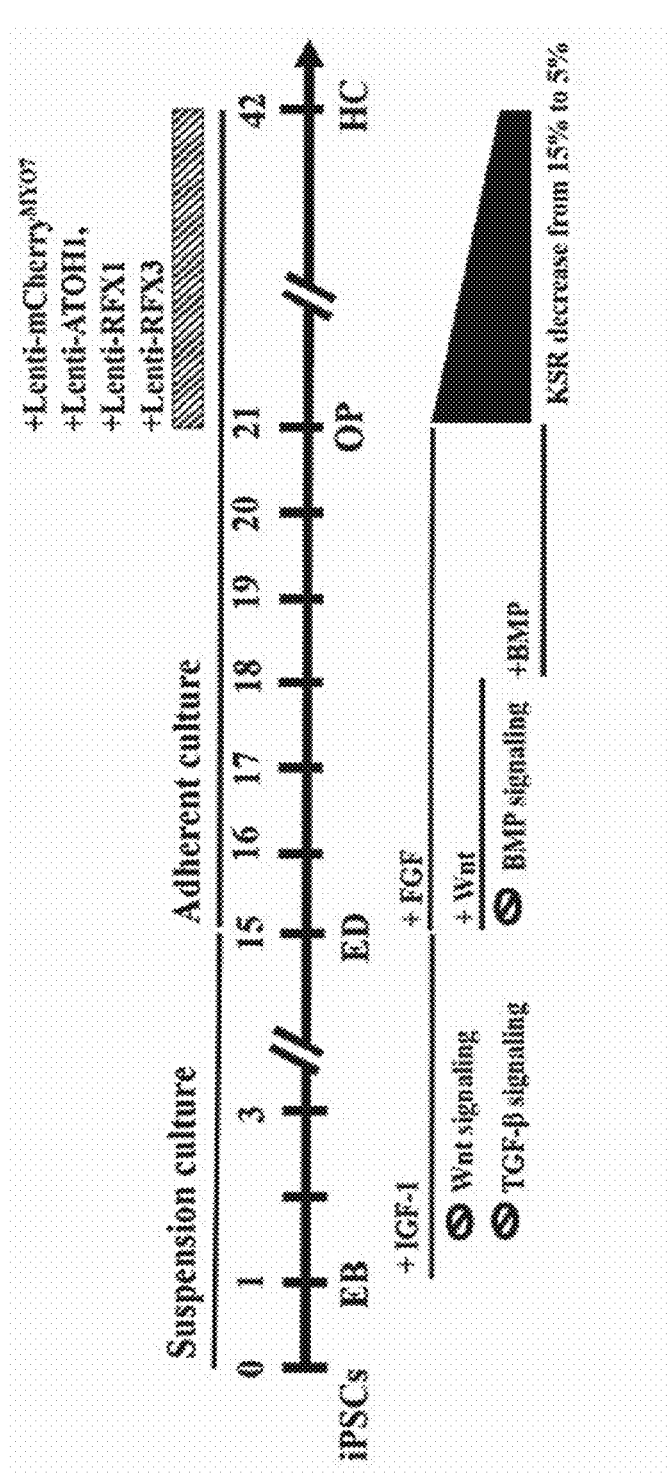
FIGS. 6A to 6G show characterisation of HC-like cells derived from MERRF-iPSCs by ATOH1/RFX1/RFX3 TFs- 5                                                                 6 driven differentiation.

Example 6: ATOH1, RFX1 and RFX3 Promote the Differentiation of HC-Like Cells and the Formation of Stereociliary Bundles Six groups of different TFs were used for differentiation: control (CTL), ATOH1, RFX1, RFX3, RFX1/RFX3, and ATOH1/RFX1/RFX3. The MYO7A$^{mCherry}$ reporter gene was used to monitor the process of HC differentiation (FIG. 6A).

Figure 6B:
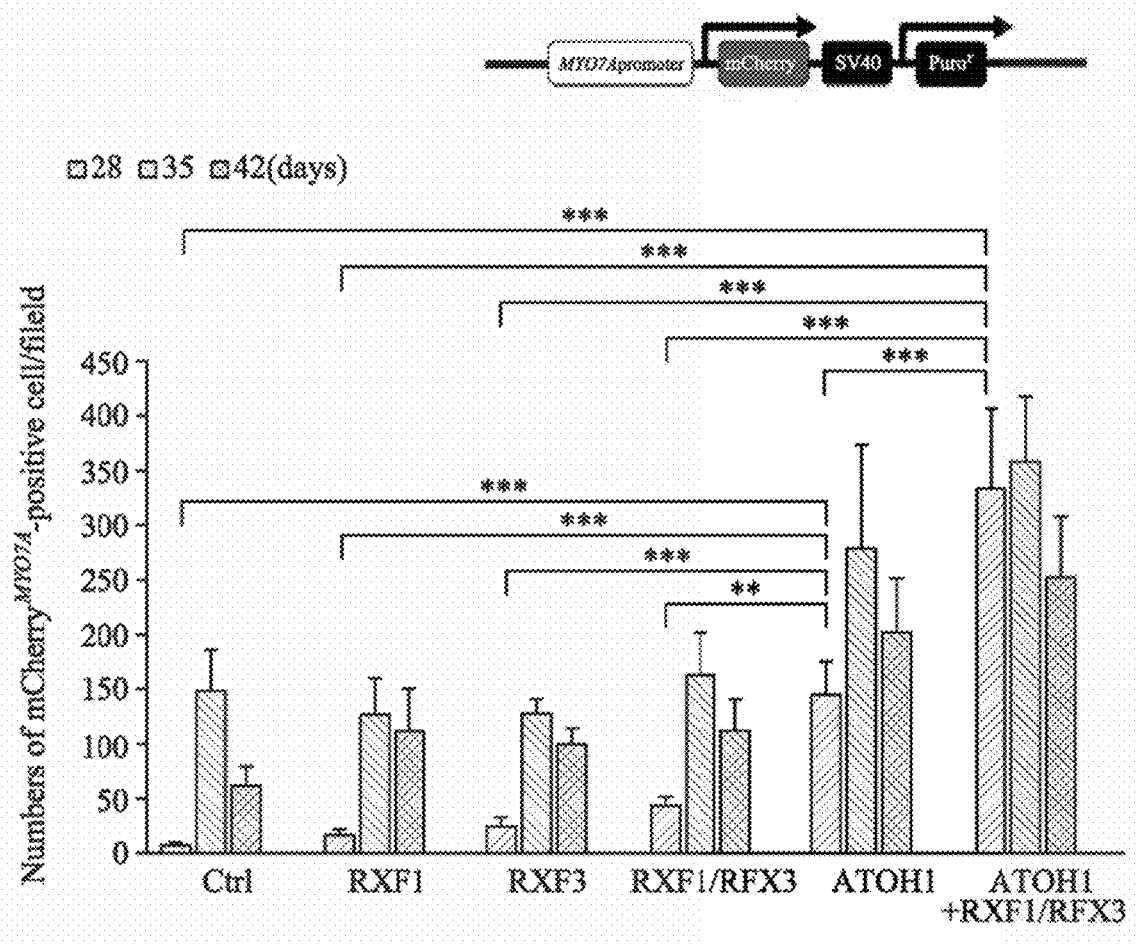

The ATOH1/RFX1/RFX3 group efficiently promoted the differentiation of iPSCs into MYO7A$^{mCherry}$-positive cells more than ATOH1 alone in the early stage of HC differentiation on Day 28 (FIG. 6B). Furthermore, ATOH1 and ATOH1/RFX1/RFX3 treatments resulted in significantly higher numbers of MYO7A$^{mCherry}$-positive cells than the CTL condition on Day 28 (FIG. 6B); however, the RFX1/RFX3 condition did not significantly increase the number of MYO7A$^{mCherry}$-positive cells. The presence of RFX1/RFX3 alone was insufficient to promote inner ear HC differentiation. By contrast, ATOH1 gene infection alone or in combination with RFX1/RFX3 at the OP stage could significantly increase the number of MYO7A$^{mCherry}$-positive cells on Day 28, implying that the decline of ATOH1 mRNA expression from the OP to HC stage (FIG. 1B) could be compensated by the infection of lenti-ATOHJ at the OP stage (FIG. 6B).

Figure 6C:
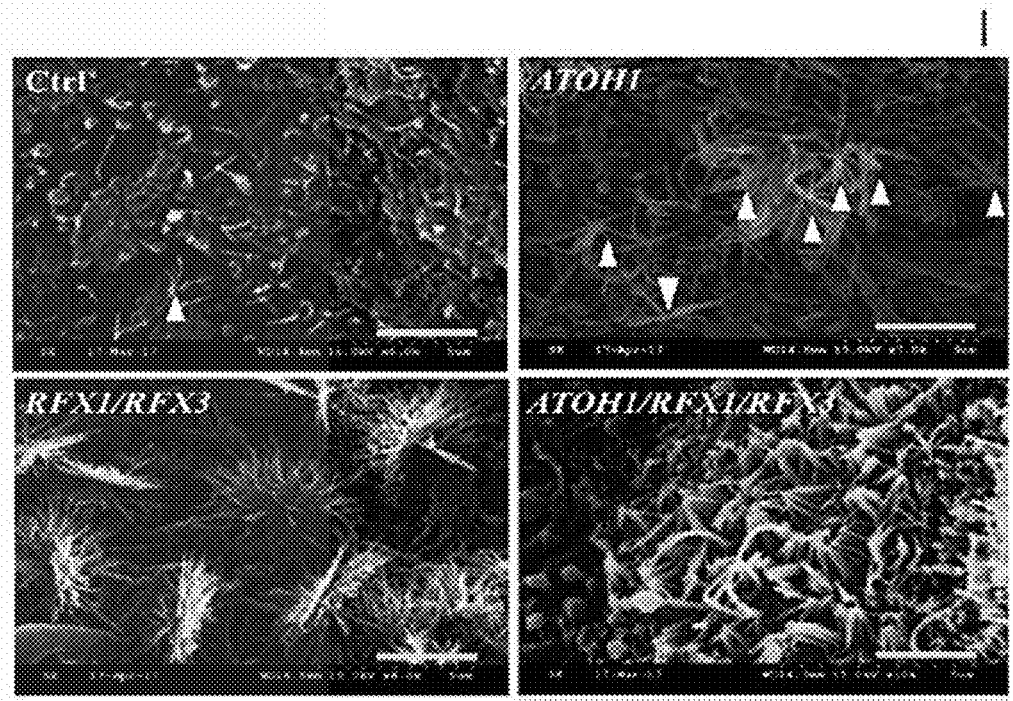
Figure 6D:
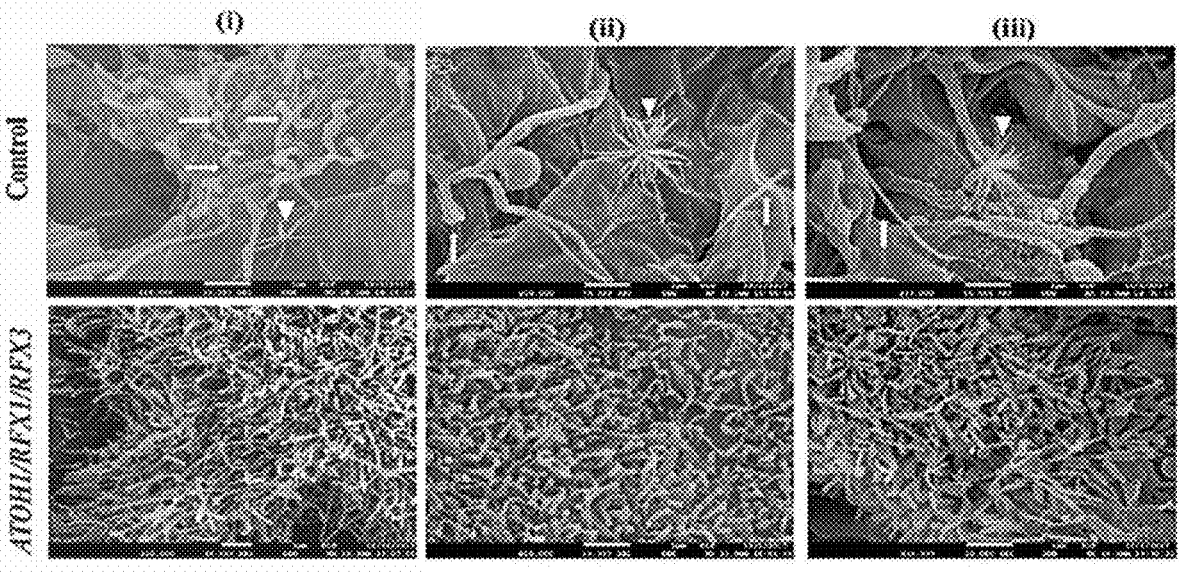
Figure 6E:
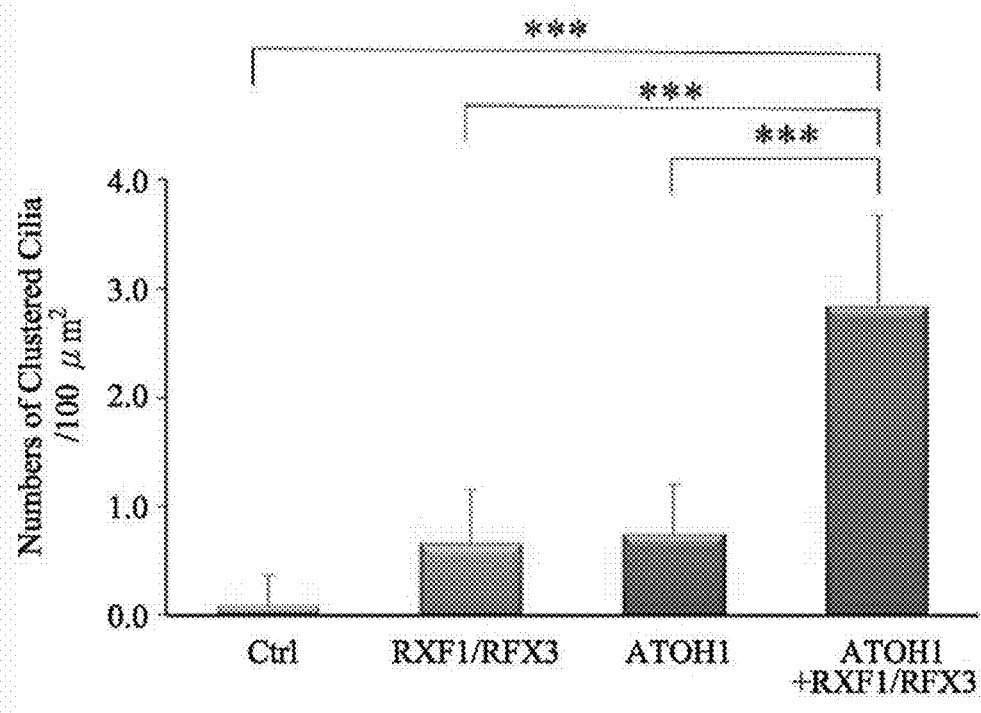
Figure 6F:
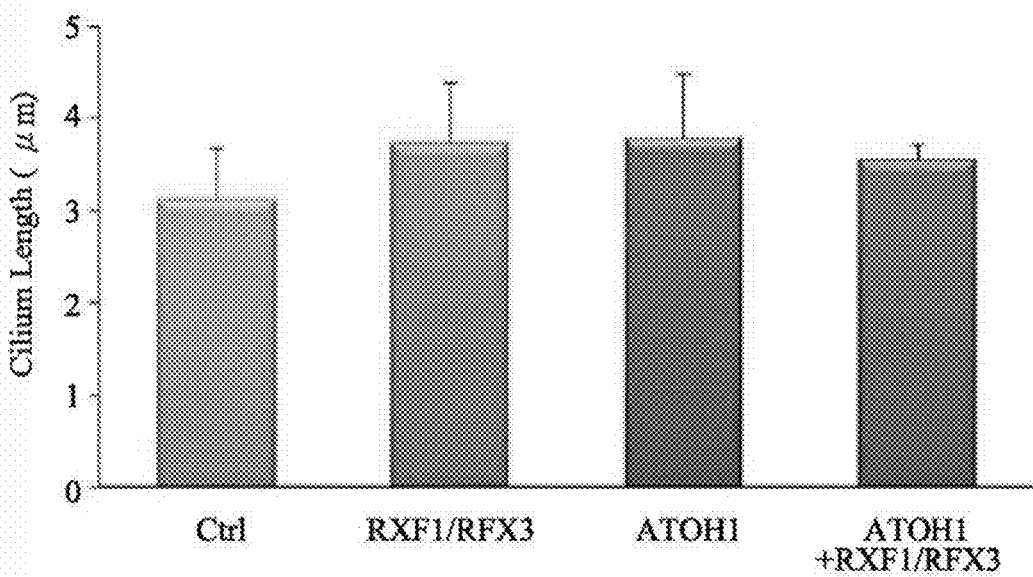

The morphology of HC-like cells derived from hiPSCs under four conditions was examined through SEM to investigate whether ATOH1/RFX1/RFX3 could promote the differentiation of HC-like cells. In the Ctrl condition, only a few single cilia on the surface of cells were observed. HC-like cells in the ATOH1 condition harboured tightly squeezed cilia on the cell surface, and a considerable number of cilia were observed. The morphology of the cilia in HC-like cells in the RFX1/RFX3 condition was clustered; however, the clustered cilia were splayed. In particular, the cilium morphology of HC-like cells in the ATOH1/RFX1/RFX3 condition exhibited stereociliary bundle-like protrusions (FIGS. 6C and 6D). The density of the clustered stereocilia in iPSC-derived HC-like cells was $0.1 \pm 0.3/100$ μm$^2$ in the Ctrl condition, $0.7 \pm 0.5/100$ μm$^2$ in the RFX1/RFX3 condition, $0.8 \pm 0.5/100$ μm$^2$ in the ATOH1 condition, and $2.8 \pm 0.8/100$ μm$^2$ in the ATOH1/RFX1/RFX3 condition (FIG. 6E). However, the cilium length in each condition was similar: $3.1 \pm 0.5$ μm in the Ctrl condition, $3.7 \pm 0.7$ μm in the RFX1/RFX3 condition, $3.8 \pm 0.7$ μm in the ATOH1 condition, and $3.5 \pm 0.2$ μm in the ATOH1/RFX1/RFX3 condition (FIG. 6F).

Figure 6G:
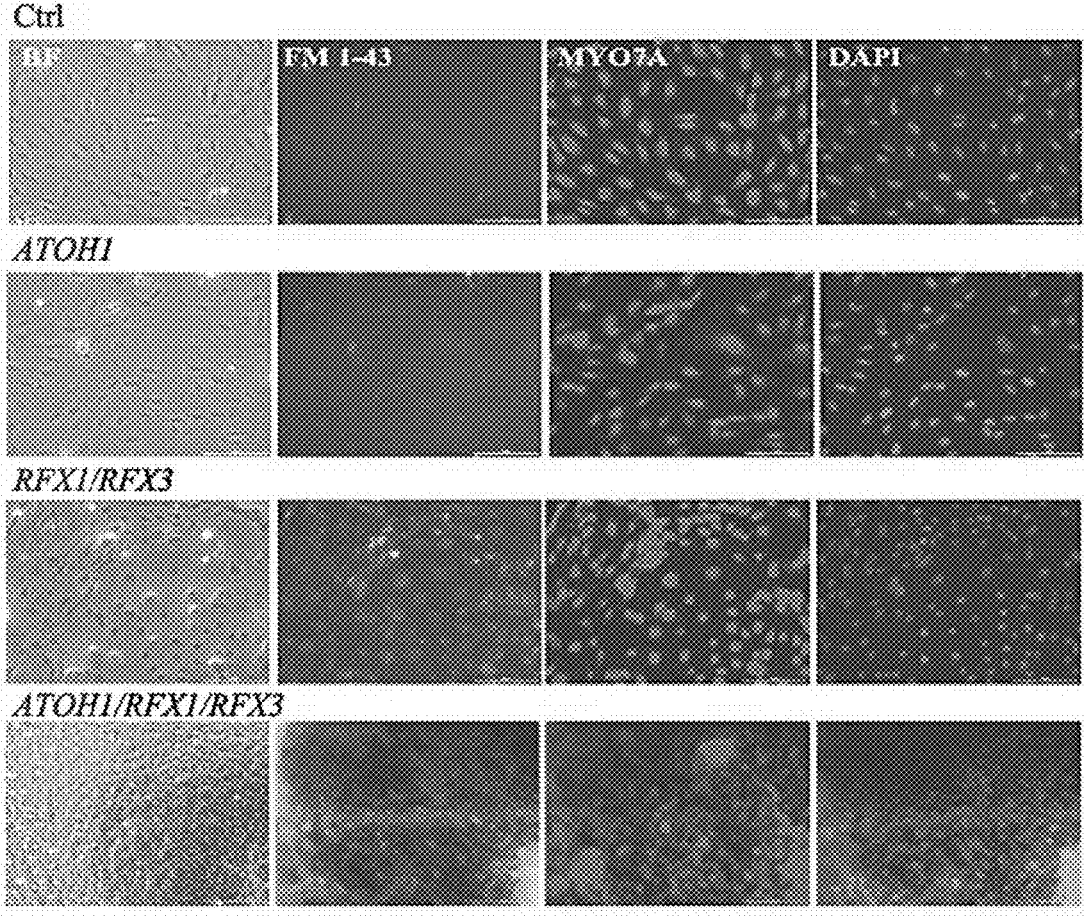

Furthermore, the expression of classic HC marker genes including MYO7A and ESPN of the cells in the four groups were analysed by immunofluorescence staining. Notably, the expression levels of FM 1-43 in the RFX1/RFX3 and ATOH1/RFX1/RFX3 conditions were markedly higher than those in the Ctrl and ATOH1 conditions, and the expression levels of MYO7A in the ATOH1/RFX1/RFX3 condition were higher than those in the Ctrl, ATOH1, and RFX1/RFX3 conditions (FIG. 6G).

17
18

Figure 7A:
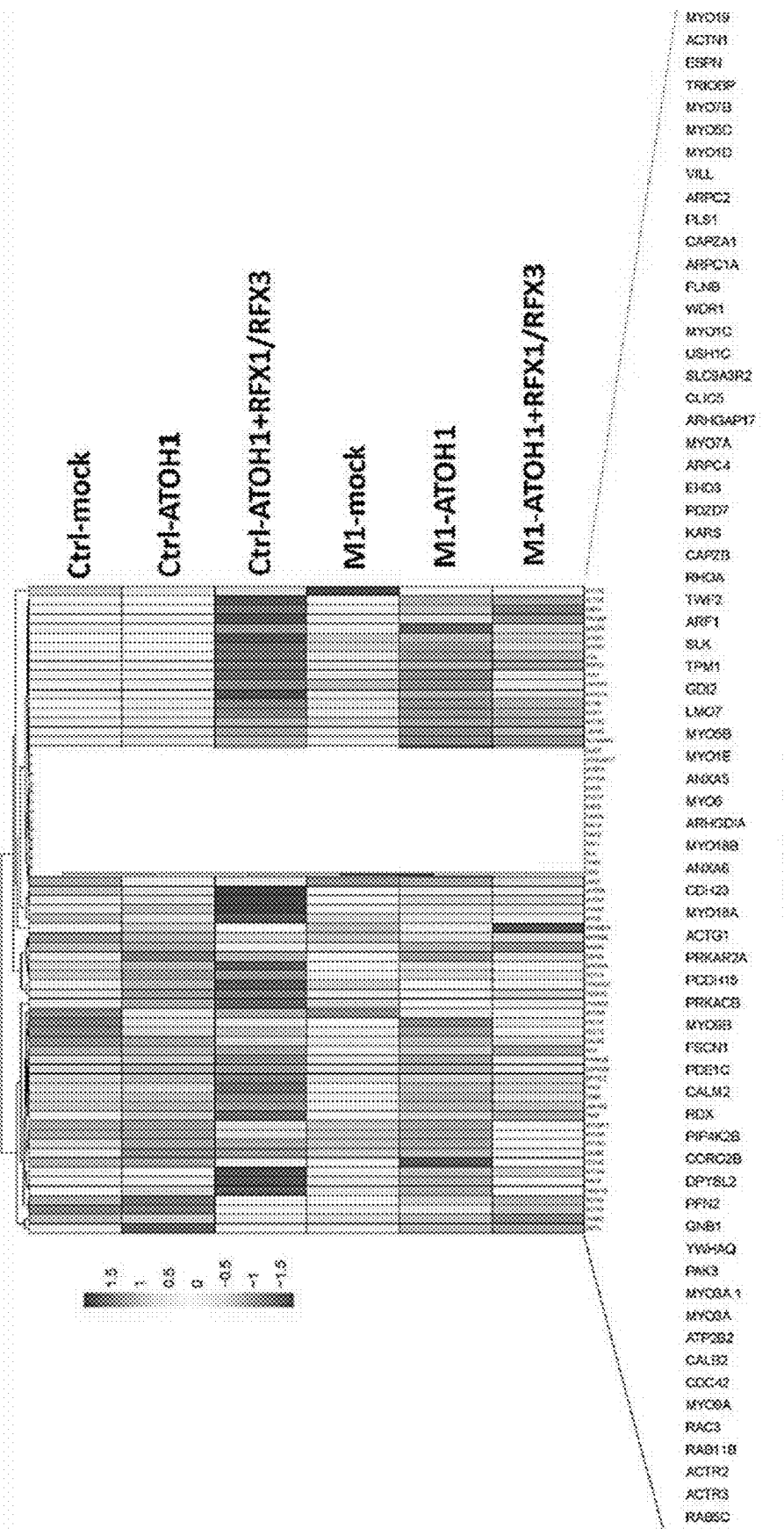
FIG. 7A shows transcriptome analyses for the genes involved in stereociliary bundles of HC-like cells differentiated from human iPSCs through an ATOH1/RFX1/RFX3 TF-driven approach by RNA-sequencing. The genes involved in the characteristics of stereociliary bundles were chosen for the cluster analyses.

Example 7: Whole Transcriptome Analysis of HC-Like Cells Differentiated from hiPSCs by RNA-Sequencing For whole transcriptome analysis, a total of 16,272 mRNA were identified as being differentially expressed (DE) when a significance threshold of P<0.05 was exclusively considered. Notably, 70 of these 16,272 mRNA-encoding genes were identified as being involved in the formation of stereociliary bundles of HCs (FIG. 7A). These results indicated that ATOH1/RFX1/RFX3 could enhance the mRNA expression of a cluster of genes involved in stereociliary bundles, including ESPN and MYO7A.

Figure 7B:
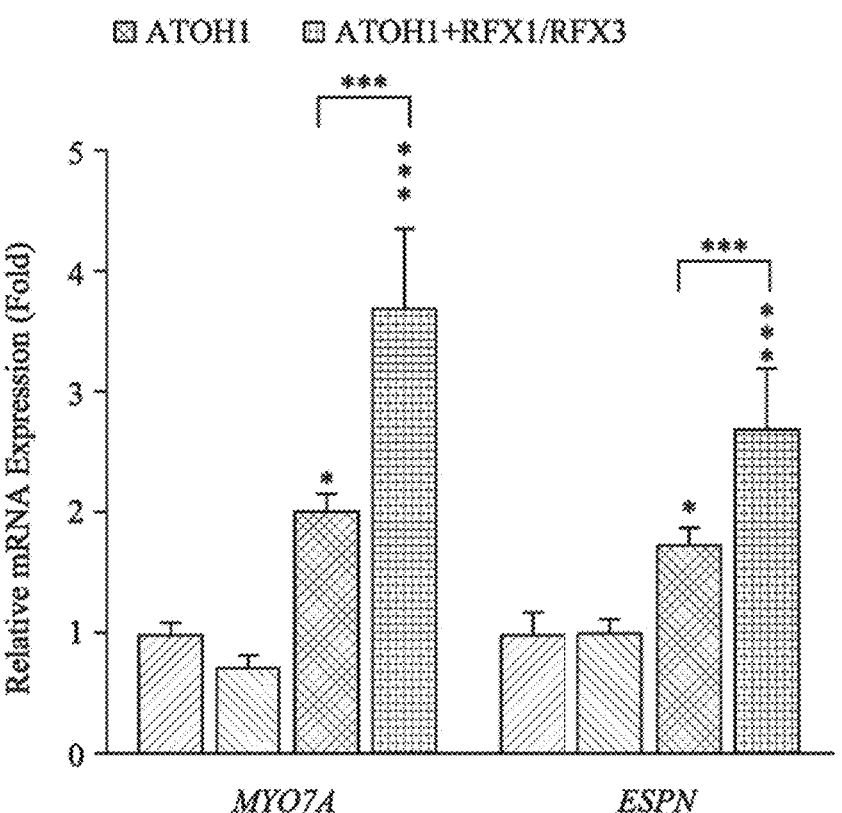
FIG. 7B shows quantitative RT-PCR analyses revealing significantly higher mRNA expression levels of MYO7A and ESPN in the ATOH1/RFX1/RFX3 and ATOH1 conditions than in the Ctrl condition. Furthermore, mRNA expression levels of MYO7A and ESPN in the ATOH1/RFX1/RFX3 condition were significantly higher than those in the ATOH1 condition. Data are presented as mean±SD. N=3, *, p<0.05, , p<0.01, *, p<0.001.

Furthermore, quantitative RT-PCR was used to demonstrate that the expression levels of MYO7A and ESPN genes in the ATOH1/RFX1/RFX3 condition were significantly higher than those in the Ctrl condition (FIG. 7B). Taken together, these findings suggest that ATOH1/RFX1/RFX3 could upregulate HC marker gene expression and promote the differentiation of HC-like cells.

Example 8: Disease Modeling of HC Dysfunction in Patients with MERRF Syndrome Differentiation capacities of M1-iPSCs and M2-iPSCs were analysed to evaluate the hiPSCs with the mtDNA A8344G mutation in HC differentiation. M1-iPSCs and M2-iPSCs were initially subjected to HC differentiation through a non-TF method. During the differentiation process, the EB formation, ectoderm induction, OP induction, and HC differentiation stages in M1-iPSCs and M2-iPSCs exhibited no differences compared with those in M1$^{ctrl}$-iPSCs (FIG. 5A).

Figure 5G:
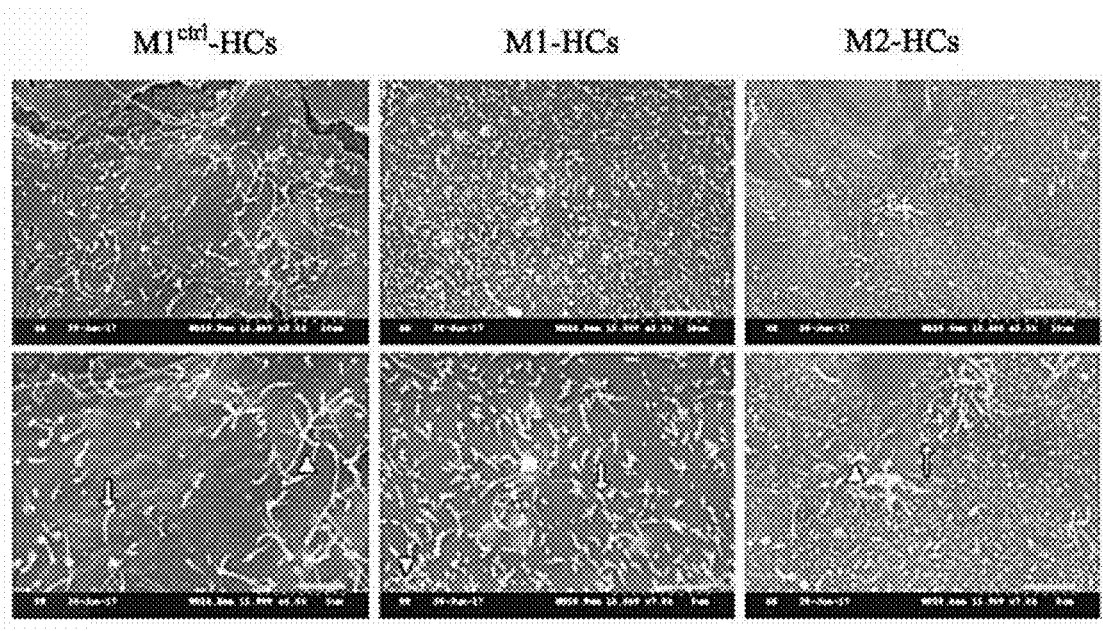
Figure 5H:
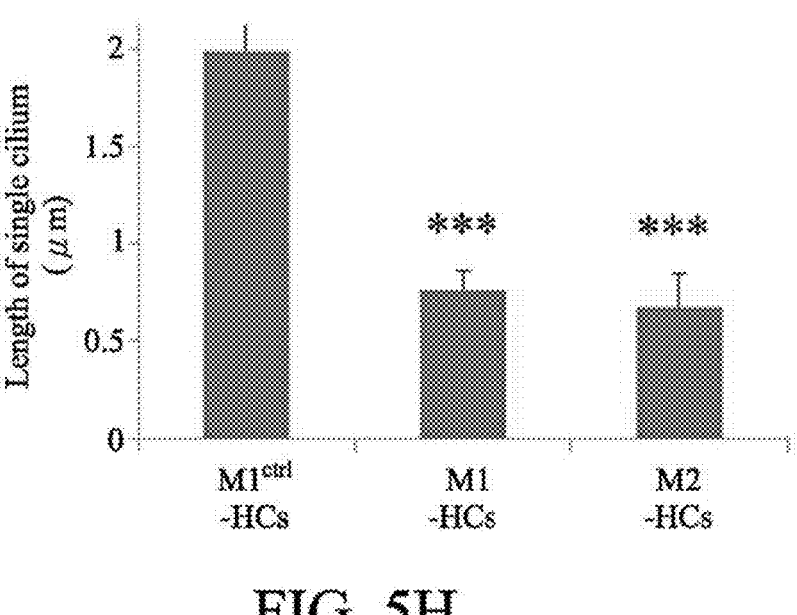
Figure 5I:
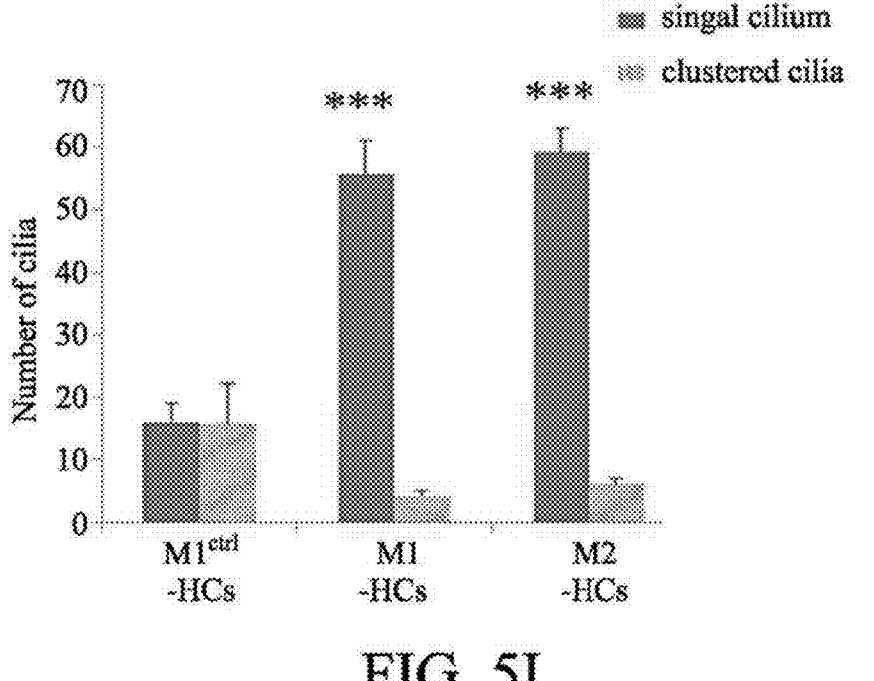
Figure 8A:
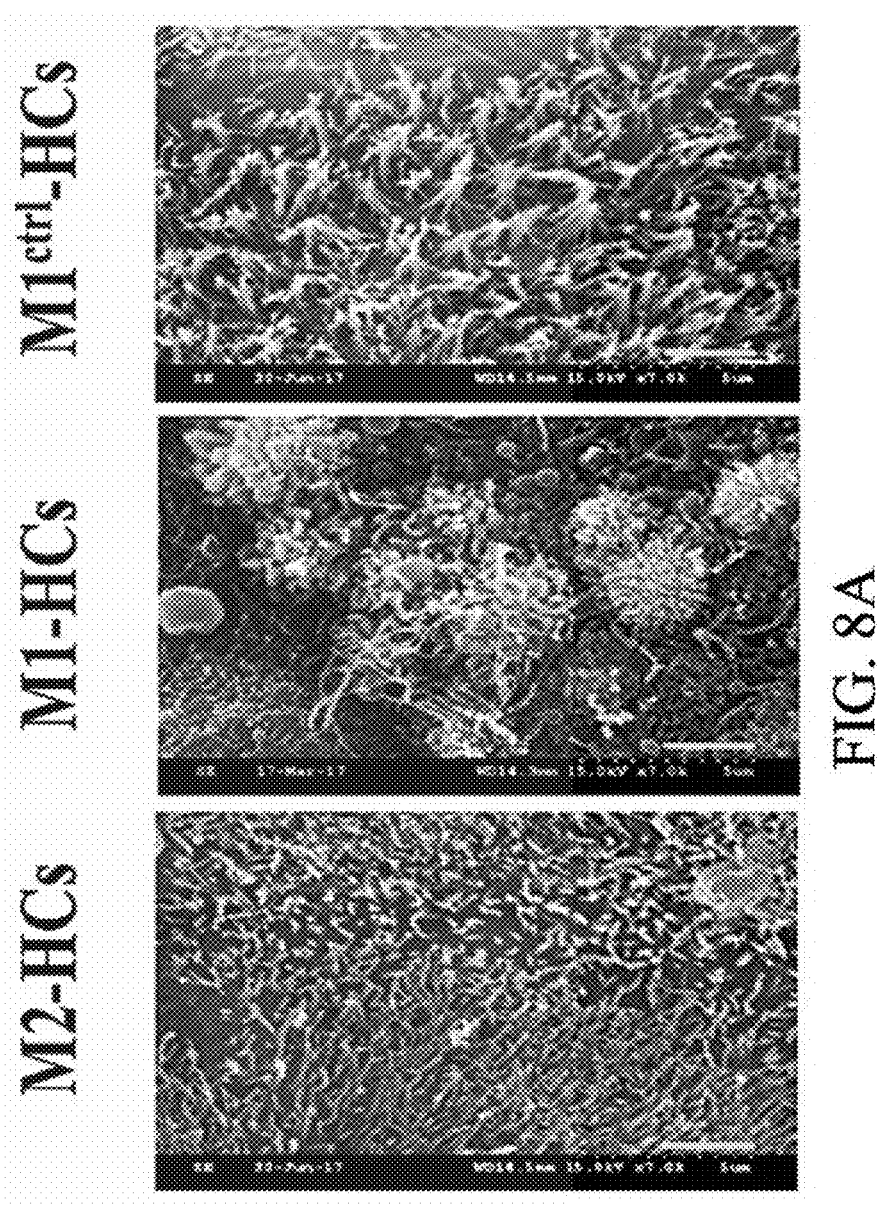
FIGS. 8A and 8B show stereociliary structure and molecular characterization of HC-like cells differentiated from MERRF-iPSCs through an ATOH1/RFX1/RFX3 TF-driven approach.
Figure 8B:
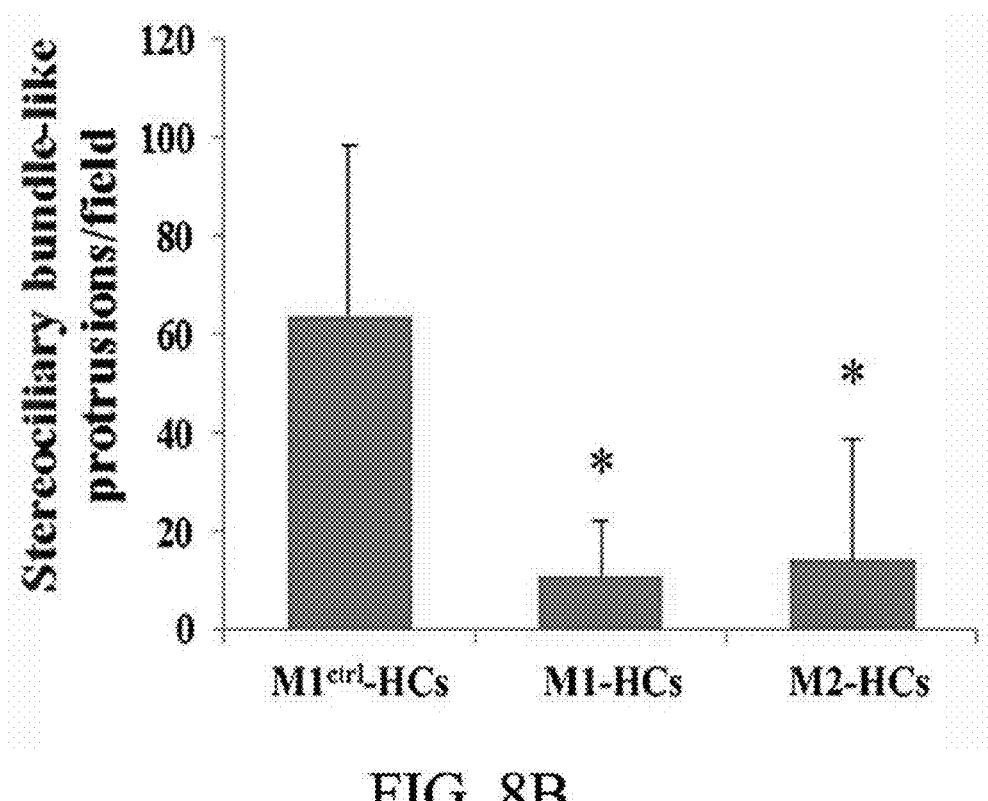

The non-TF-method-differentiated HC-like cells derived from M1-iPSCs and M2-iPSCs also exhibited a single cilium (arrows) or a cluster of cilia (arrowheads), and the clustered cilia were splayed and did not closely resemble the typical morphology of the stereociliary bundles of HCs (FIG. 5G). MERRF-HC-like cells that had more single cilia with a shorter length could be observed using the non-TF method (FIGS. 5H and 5I), and those with fewer stereociliary bundle-like protrusions than the control HC-like cells could be further observed using ATOH1/RFX1/RFX3 TFs (FIGS. 8A and 8B).

While some of the embodiments of the present disclosure have been described in detail in the above, it is, however, possible for those of ordinary skill in the art to make various modifications and changes to the particular embodiments shown without substantially departing from the teaching and advantages of the present disclosure. Such modifications and changes are encompassed in the spirit and scope of the present disclosure as set forth in the appended claim.

REFERENCES

1. Jeon S J, Oshima K, Heller S, Edge A S. Bone marrow mesenchymal stem cells are progenitors in vitro for inner ear hair cells. Mol. Cell. Neurosci. 2007; 34: 59-68.
2. Beisel K, Hansen L, Soukup G, Fritzsch B. Regenerating cochlear hair cells: quo vadis stem cell. Cell Tissue Res. 2008; 333: 373-379.
3. Oshima K, Shin K, Diensthuber M, Peng A W, Ricci A J, Heller S. Mechanosensitive hair cell-like cells from embryonic and induced pluripotent stem cells. Cell. 2010; 141: 704-716.
4. Ronaghi M, Nasr M, Ealy M, Durruthy-Durruthy R, Waldhaus J, Diaz G H, et al. Inner ear hair cell-like cells from human embryonic stem cells. Stem Cells Dev. 2014; 23: 1275-1284.
5. Schimmang T. Transcription factors that control inner ear development and their potential for transdifferentiation and reprogramming Hear Res. 2013; 297: 84-90.
6. Devarajan K, Forrest M L, Detamore M S, Staecker H. Adenovector-mediated gene delivery to human umbilical cord mesenchymal stromal cells induces inner ear cell phenotype. Cell Reprogram. 2013; 15: 43-54.
7. Atkinson P J, Wise A K, Flynn B O, Nayagam B A, Richardson R T. Hair cell regeneration after ATOH1 gene therapy in the cochlea of profoundly deaf adult guinea pigs. PLoS One. 2014; 9: e102077.
8. Yang S M, Chen W, Guo W W, Jia S, Sun J H, Liu H Z, et al. Regeneration of stereocilia of hair cells by forced Atoh1 expression in the adult mammalian cochlea. PLoS One. 2012; 7: e46355.
9. Izumikawa M, Minoda R, Kawamoto K, Abrashkin K A, Swiderski D L, Dolan D F, et al. Auditory hair cell replacement and hearing improvement by Atoh1 gene therapy in deaf mammals. Nat. Med. 2005; 11: 271-276.
10. A Three-part, Multicenter, Open Label, Single Dose Study to Assess the Safety, Tolerability, and Efficacy of Intra Labyrinthine (I L) CGF166 in Patients With Severe-to-profound Hearing Loss: Novartis Pharmaceuticals 2017.
11. Liu Z, Fang J, Dearman J, Zhang L, Zuo J. In vivo generation of immature inner hair cells in neonatal mouse cochleae by ectopic Atoh1 expression. PLoS One. 2014; 9: e89377.
12. Purvis T L, Hearn T, Spalluto C, Knorz V J, Hanley K P, Sanchez-Elsner T, et al. Transcriptional regulation of the Alstrom syndrome gene ALMS1 by members of the RFX family and Sp1. Gene. 2010; 460: 20-29.
13. Lubelsky, Y, Reuven, N, Shaul, Y. Autorepression of rfxl gene expression: functional conservation from yeast to humans in response to DNA replication arrest. Mol. Cell Biol. 25, 10665-10673 (2005).
14. Iwama, A. et al. Dimeric RFX proteins contribute to the activity and lineage specificity of the interleukin-5 receptor alpha promoter through activation and repression domains. Mol. Cell Biol. 19, 3940-3950 (1999).
15. Chou, S. J. et al. Impaired ROS scavenging system in human induced pluripotent stem cells generated from patients with MERRF syndrome. Sci. Rep. 6: 23661 (2016).
16. Boyer, L. A. et al. Core transcriptional regulatory circuitry in human embryonic stem cells. Cell 122: 947-956 (2005).
17. Kiernan, A. E. et al. Sox2 is required for sensory organ development in the mammalian inner ear. Nature. 434: 1031-1035 (2005).
18. Boeda, B., Weil, D., Petit, C. A specific promoter of the sensory cells of the inner ear defined by transgenesis. Hum. Mol. Genet. 10: 1581-1589 (2001).

What is claimed is:

1. A method for treating hearing loss in a subject in need thereof, comprising:

providing a set of nucleic acids or a set of polypeptides;

inducing generation of a mature hair cell-like cell by culturing an otic progenitor cell in the presence of the set of nucleic acids or the set of polypeptides; and delivering the mature hair cell-like cell into an inner ear of the subject, wherein the set of nucleic acids comprises a first nucleic acid encoding ATOH1, a second nucleic acid encoding RFX1, and a third nucleic acid encoding RFX3, or wherein the set of polypeptides comprises ATOH1, RFX1, and RFX3.

2. The method according to claim 1, wherein the set of nucleic acids or the set of polypeptides increases expression levels of RFX1 and RFX3 in the otic progenitor cell.

3. The method according to claim 1, wherein the generation of the mature hair cell-like cell is driven by differentiation of an otic progenitor cell of the inner ear of the subject, or by direct reprogramming of a pluripotent stem cell derived from a somatic cell of the subject.

4. The method according to claim 3, further comprising differentiating an induced pluripotent stem cell derived from a somatic cell of the subject into the otic progenitor cell in the absence of a feeder cell.

5. The method according to claim 1, wherein the subject has myoclonus epilepsy associated with ragged-red fibres syndrome or mitochondrial mutation-associated hearing loss.

6. The method according to claim 1, wherein the subject suffers from sensorineural hearing loss, or wherein the hearing loss involves degeneration or loss of inner ear hair cells.

7. The method according to claim 1, wherein the mature hair cell-like cell has stereociliary bundles on the cell surface thereof.

8. A method of generating a mature hair cell-like cell from a pluripotent stem cell in vitro, comprising:

differentiating the pluripotent stem cell into an otic progenitor cell; and culturing the otic progenitor cell in the presence of a set of nucleic acids or a set of polypeptides to obtain a population comprising the mature hair cell-like cell, wherein the set of nucleic acids comprises a first nucleic acid encoding ATOH1, a second nucleic acid encoding RFX1, and a third nucleic acid encoding RFX3, and wherein the set of polypeptides comprises ATOH1, RFX1, and RFX3.

9. The method according to claim 8, wherein the set of nucleic acids or the set of polypeptides increases expression levels of RFX1 and RFX3 in the otic progenitor cell.

10. The method according to claim 8, wherein the otic progenitor cell is cultured in the absence of a feeder cell to obtain the population comprising the mature hair cell-like cell.

11. The method according to claim 8, wherein the mature hair cell-like cell is positive for at least one of myosin 7$a$ and espin.

12. The method according to claim 8, wherein the pluripotent stem cell is a human induced pluripotent stem cell derived from a somatic cell of a subject suffering from sensorineural hearing loss or suffering from hearing loss involving degeneration or loss of inner ear hair cells.

13. The method according to claim 8, wherein the pluripotent stem cell is a human induced pluripotent stem cell derived from a somatic cell.

\*    \*    \*    \*    \*